(12) United States Patent
Isobe et al.

(10) Patent No.: US 9,091,692 B2
(45) Date of Patent: Jul. 28, 2015

(54) FLUORESCENT DYE

(75) Inventors: Shinichiro Isobe, Fukuoka (JP); Shuntaro Mataka, Fukuoka (JP)

(73) Assignee: SHINICHIRO ISOBE, Fukuoka (JP)

( * ) Notice: Subject to any disclaimer, the term of this patent is extended or adjusted under 35 U.S.C. 154(b) by 0 days.

(21) Appl. No.: 13/985,098

(22) PCT Filed: Feb. 18, 2011

(86) PCT No.: PCT/JP2011/053503
§ 371 (c)(1),
(2), (4) Date: Mar. 25, 2014

(87) PCT Pub. No.: WO2012/111142
PCT Pub. Date: Aug. 23, 2012

(65) Prior Publication Data
US 2014/0206872 A1  Jul. 24, 2014

(51) Int. Cl.
*G01N 33/58*  (2006.01)
*C07D 498/04*  (2006.01)
*C07D 513/04*  (2006.01)
*C09B 69/00*  (2006.01)
*G01N 33/533*  (2006.01)

(52) U.S. Cl.
CPC ............ *G01N 33/582* (2013.01); *C07D 498/04* (2013.01); *C07D 513/04* (2013.01); *C09B 69/001* (2013.01); *G01N 33/533* (2013.01)

(58) Field of Classification Search
CPC .................................................. C07D 401/14
USPC .................................. 546/114, 115, 118, 119
See application file for complete search history.

(56) References Cited

FOREIGN PATENT DOCUMENTS

| JP | 2005-258388 |   | 9/2005 |
|---|---|---|---|
| JP | 2008-156556 |   | 7/2008 |
| JP | 2008156556 | * | 7/2008 |
| JP | 2008184592 | * | 8/2008 |
| JP | 2010037511 | * | 8/2008 |
| JP | 2010-37511 |   | 2/2010 |

OTHER PUBLICATIONS

International Search Report issued May 17, 2011 in International (PCT) Application No. PCT/JP2011/053503.
Iyer et al., "The Transcriptional Program in the Response of Human Fibroblasts to Serum", Science, vol. 283, Jan. 1, 1999, pp. 83-87.
Zhu et al., "The determination of thiols based using a probe that utilizes both an absorption red-shift and fluorescence enhancement", Dyes and Pigments, vol. 86, 2010, pp. 87-92.
English translation of International Preliminary Report on Patentability and Written Opinion dated Sep. 3, 2013.

* cited by examiner

*Primary Examiner* — Niloofar Rahmani
(74) *Attorney, Agent, or Firm* — Wenderoth, Lind & Ponack, L.L.P.

(57) ABSTRACT

There is provided a fluorescent dye which can improve the fluorescent intensity at the time of labeling to thereby detect a biomolecule with higher sensitivity. The fluorescent dye of the present invention includes a nitrogen cation-containing group or a nitrogen-containing group. Its high water solubility can improve the rate of labeling for a biomolecule to thereby detect a biomolecule with high sensitivity.

4 Claims, 1 Drawing Sheet

FLUORESCENT DYE

TECHNICAL FIELD

The present invention relates to a fluorescent dye which is used to detect biomolecules such as nucleic acid, protein, peptides, and saccharides, emits light, and has water solubility.

BACKGROUND ART

In recent years, the whole contents of the human genome have been clarified and post genome studies have been enthusiastically made for the purposes of executing gene therapy, genetic diagnosis and the like. For example, in DNA analysis, a DNA probe fixed onto a DNA microarray substrate is hybridized with a sample DNA labeled by a fluorescent dye or the like to form a double stranded DNA, thereby detecting the sample DNA. This is a technique in which measurement is made after a nucleic acid labeled by a fluorescent dye is PCR-extended and hybridized on a substrate. In these days, a technique using a primer having more amino groups and a technique in which an amino group is introduced into DNA are used.

A fluorescent dye is widely used for labeling and is required to have high fluorescent intensity, to emit light even in a dry state (solid state), to have water solubility, and the like. As the fluorescent dye, for example, Cy3 or Cy5 is used (for example, Non-patent Document 1).

Non-Patent Document 1: Science 283, 1, January, 1999, 83-87

DISCLOSURE OF THE INVENTION

Problem to be Solved by the Invention

However, a fluorescent dye which emits light even in a dry state is oil-soluble, giving rise to a problem concerning low water-solubility. For this reason, the fluorescent dye can be insufficiently dissolved in a sample solution and the labeling rate is not raised, with the result that sufficient fluorescence intensity is not obtained.

Solutions to the Problem

In order to solve the above problem, a fluorescent dye according to one aspect of the present invention comprises an azole derivative represented by the following general formula (1), (2), or (3):

[Chemical Formula 1]

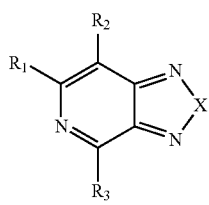

(1)

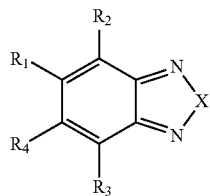

(2)

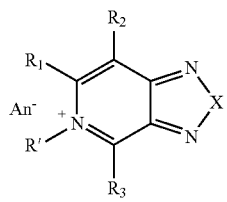

(3)

$R_1$ in the formulae (1) and (3) and one of $R_1$ and $R_4$ in the formula (2) are each represented by the general formula $L_1$-$M_1$, wherein $M_1$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_1$ represents a linker which is represented by —(CH=$CR_6$)$_n$— and which connects $M_1$ with a center pyridine ring or a center benzene ring, n represents an integer of from 1 to 5, $R_6$ represents any one of a hydrogen atom; a linear or branched alkyl group which may have a substituent and has 1 to 6 carbon atoms; a sulfo group which may have a substituent; a heterocyclic group selected from the group consisting of an imidazolium group, a pyridinium group, and a furan group, each of which may have a substituent; an amino group selected from the group consisting of a secondary amino group, a tertiary amino group, and a quaternary amino group, each of which may have a substituent; a hydroxy group which may have a substituent; an alkoxy group which may have a substituent; an aldehyde group which may have a substituent; a carboxyl group which may have a substituent; and an aromatic group which may have a substituent, the residues of $R_1$ and $R_4$ in the formula (2) and $R_2$ and $R_3$ in the formulae (1) to (3) each independently represent a hydrogen atom, a halogen atom, or an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and An⁻ represents a halide ion, $CF_3SO_3^-$, $BF_4^-$, or $PF_6^-$.

A fluorescent dye according to another aspect of the present invention comprises an azole derivative represented by the following general formula (4), (5), or (6).

[Chemical Formula 2]

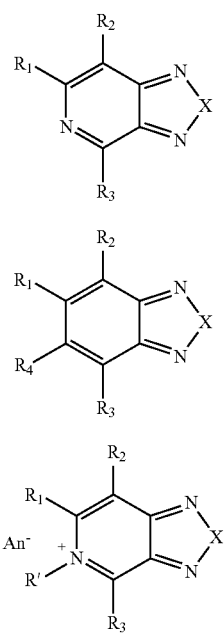

$R_1$ in the formulae (4) and (6) and one of $R_1$ and $R_4$ in the formula (5) are each represented by the general formula $L_2$-$M_2$, wherein $M_2$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_2$ represents a linker which connects $M_2$ with a center pyridine ring or a center benzene ring and which represents a direct bond or one or more types of functional groups selected from the group consisting of —$(CH_2)_n$— (n represents an integer of from 1 to 4), —NHCOO—, —CONH—, —COO—, —$SO_2$NH—, —HN—C(=NH)—NH—, —O—, —S—, —NR (R represents an alkyl group), —Ar— (Ar represents an aromatic hydrocarbon group), and —CO—Ar—NR—, the residues of R, and $R_4$ in the formula (5) and $R_2$ and $R_3$ in the formulae (4) to (6) each independently represent a thienyl group, a furanyl group, a pyrrolyl group, an imidazolyl group, an oxazolyl group, a thiadiazolyl group, a pyrazolyl group, a pyridyl group, or a quinolyl group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and $An^-$ represents a halide ion, $CF_3SO_3^-$, $BF_4^-$, or $PF_8^-$.

Effects of the Invention

The fluorescent dye of the present invention is an organic EL dye including an azole derivative which has a conjugated system and contains one or more types of hetero atoms, selenium atoms, or boron atoms, the fluorescent dye having a nitrogen cation-containing group or a nitrogen-containing group. Its high water solubility can improve the rate of labeling for a biomolecule to thereby detect a biomolecule with high sensitivity. This can remarkably reduce the amount of a fluorescent dye to be used, and it is therefore also possible to largely decrease the cost for detecting a target molecule. Because an organic EL dye has a high quantum yield in a solid state (including solid and semisolid state), it gives high fluorescent intensity even in a dry state on a substrate such as a microarray or on beads. The organic EL dye is inexpensive as compared with Cy3 and Cy5, and therefore a biomolecule can be detected at a lower cost. Because excitation wavelength and emission wavelength can be altered by changing the substituent of the organic EL dye, the degree of freedom of choice in fluorescent wavelength is increased, and therefore many fluorescent wavelength such as red, orange, yellow, green, and blue can be used. This enables the use of two or more types of fluorescent dyes having a large stokes shift (large difference between excitation wavelength and fluorescent wavelength) and also enables the simultaneous detection of a plurality of target nucleic acids contained in one sample. Further, though it is necessary that Cy3 and Cy5 be subjected to cryopreservation, the organic EL dye is chemically stable so that it can stand against long-term storage at normal temperature, and it is therefore easily handled.

BEST MODE FOR CARRYING OUT THE INVENTION

Figure 1:
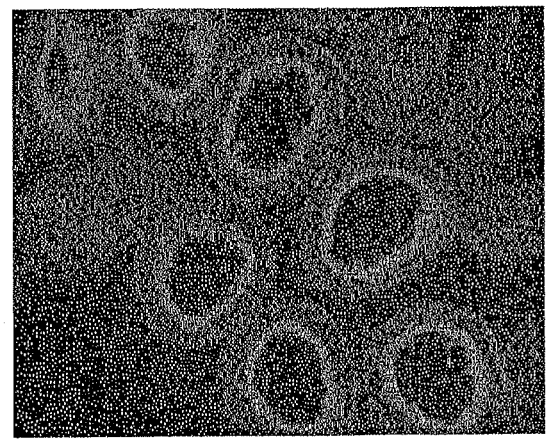
FIG. 1 is a fluorescence micrograph of a specimen produced using a fluorescent dye according to the present invention.

An embodiment of the present invention will be described in detail.

Embodiment 1

A fluorescent dye according to this embodiment is a fluorescent dye including an azole derivative and may be represented by the following formulae (1), (2) and (3).

[Chemical Formula 3]

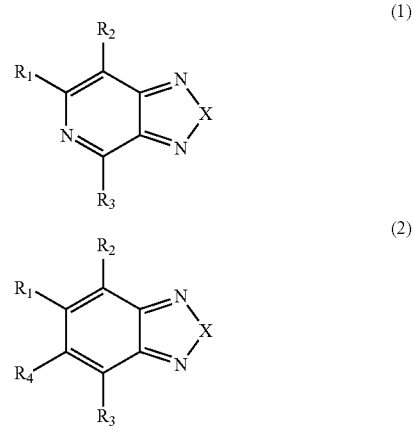

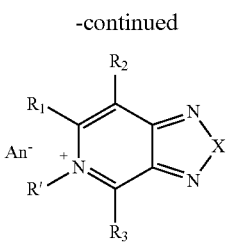

(3)

R₁ in the formulae (1) and (3) and one of R₁ and R₄ in the formula (2) are each represented by the general formula $L_1$-$M_1$, wherein $M_1$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_1$ represents a linker which is represented by —(CH═CR₆)ₙ— and which connects $M_1$ with a center pyridine ring or a center benzene ring, n represents an integer of from 1 to 5, $R_6$ represents any one of a hydrogen atom; a linear or branched alkyl group which may have a substituent and has 1 to 6 carbon atoms; a sulfo group which may have a substituent; a heterocyclic group selected from the group consisting of an imidazolium group, a pyridinium group, and a furan group, each of which may have a substituent; an amino group selected from the group consisting of a secondary amino group, a tertiary amino group, and a quaternary amino group, each of which may have a substituent; a hydroxy group which may have a substituent; an alkoxy group which may have a substituent; an aldehyde group which may have a substituent; a carboxyl group which may have a substituent; and an aromatic group which may have a substituent, the residues of $R_1$ and $R_4$ in the formula (2) and $R_2$ and $R_3$ in the formulae (1) to (3) each independently represent a hydrogen atom, a halogen atom, or an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and An⁻ represents a halide ion, $CF_3SO_3^-$, $BF_4^-$, or $PF_6^-$. The linker reduces a steric hindrance between a color developing part and a biomolecule which is an object to be labeled to make it easy to bind the connected part with the labeled part of the biomolecule, and therefore it is possible to give a high labeling rate.

$R_2$ and $R_3$ are each independently preferably an aromatic hydrocarbon group, an aliphatic hydrocarbon group, or a heterocyclic group, each of which may have a substituent. Examples of the substituent may include: an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms. The aromatic hydrocarbon group as the substituent is an aryl group containing a monocycle or polycycle. The heterocyclic group as the substituent is, for example, a thienyl group, a furanyl group, a pyrrolyl group, an imidazolyl group, an oxazolyl group, a thiadiazolyl group, a pyrazolyl group, a pyridyl group, or a quinolyl group. $R_2$ and $R_3$ may each be an aryl group having a sulfonyl group.

$R_2$ and $R_3$ above are each independently preferably a thienyl group, a furanyl group, a pyrrolyl group, an imidazolyl group, an oxazolyl group, a thiadiazolyl group, a pyrazolyl group, a pyridyl group, or a quinolyl group, each of which may have a substituent. This is because the fluorescent wavelength is shifted to the large wavelength side to obtain a larger stokes shift as compared with the case of using an unsubstituted group or a phenyl group. $R_2$ and $R_3$ each more preferably represent a thienyl group which may have a substituent, wherein the substituent is an aromatic hydrocarbon group, an aliphatic hydrocarbon group, or a heterocyclic group, each of which may have a substituent.

Here, the aromatic hydrocarbon group which may have a substituent is an aryl group containing a monocycle or a polycycle, and examples of the aryl group may include a substituted or unsubstituted phenyl group, a naphthyl group, a biphenyl group and the like. In this case, the aromatic hydrocarbon group which may have a substituent may include the substituents in the number of 1 to 3. Examples of the substituents may include an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms.

Examples of the aliphatic hydrocarbon group which may have a substituent may include a substituted or unsubstituted, linear or branched alkyl group having 1 to 20 carbon atoms, an unsubstituted, linear or branched alkenyl group having 2 to 20 carbon atoms, and an unsubstituted, linear or branched alkynyl group having 2 to 20 carbon atoms and the like.

Examples of the heterocyclic group which may have a substituent may include substituted or unsubstituted furanyl group, pyrrolyl group, imidazolyl group, oxazolyl group, thiadiazolyl group, pyrazolyl group, pyridyl group, and quinolyl group.

As the substituent of the thienyl group, an aromatic hydrocarbon group or an aliphatic hydrocarbon group which may have a substituent is preferable, an aromatic hydrocarbon group which may have a substituent is more preferable, and an aryl group having a monocycle or polycycle is furthermore preferable. Specific examples may include substituted or unsubstituted phenyl group, naphthyl group, biphenyl group and the like. In this case, the aromatic hydrocarbon group which may have a substituent may include the substituents in the number of 1 to 3, and examples of the substituent may include an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms.

According to this embodiment, the fluorescent dye has high water solubility, and therefore the rate of labeling for a biomolecule can be improved to thereby detect a biomolecule with high sensitivity. The excitation wavelength and emission wavelength are altered by changing the substituent of the fluorescent dye to enable the use of two or more types of fluorescent dyes each having a large stokes shift, thereby making it possible to simultaneously detect a plurality of target molecules contained in one sample. When, particularly, a thienyl group which may have a substituent is used as $R_2$ and $R_3$, a stokes shift exceeding 100 nm is obtained, and therefore detection with high sensitivity can be performed without any influence of excitation light.

In this embodiment, though an example of a diazole derivative is shown as the azole derivative, a triazole derivative represented by the following general formula may be used. Even if a triazole derivative is used, the same effect as that of the diazole derivative can be obtained.

[Chemical Formula 4]

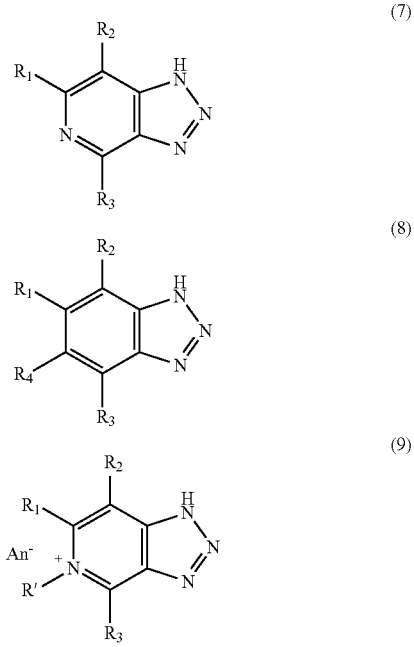

$R_1$ in the formulae (7) and (9) and one of $R_1$ and $R_7$ in the formula (8) are each represented by the general formula $L_3$-$M_3$, wherein $M_3$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_3$ represents a linker which is represented by —(CH=$CR_6$)$_n$— and which connects $M_3$ with a center pyridine ring or a center benzene ring, n represents an integer of from 1 to 5, $R_6$ represents any one of a hydrogen atom; a linear or branched alkyl group which may have a substituent and has 1 to 6 carbon atoms; a sulfo group which may have a substituent; a heterocyclic group selected from the group consisting of an imidazolium group, a pyridinium group, and a furan group, each of which may have a substituent; an amino group selected from the group consisting of a secondary amino group, a tertiary amino group, and a quaternary amino group, each of which may have a substituent; a hydroxy group which may have a substituent; an alkoxy group which may have a substituent; an aldehyde group which may have a substituent; a carboxyl group which may have a substituent; and an aromatic group which may have a substituent, the residues of $R_1$ and $R_7$ in the formula (8) and $R_2$ and $R_3$ in the formulae (7) to (9) each independently represent a hydrogen atom, a halogen atom, or an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and An$^-$ represents a halide ion, $CF_3SO_3^-$, $BF_4^-$, or $PF_6^-$.

$R_2$ and $R_3$ are each independently preferably an aromatic hydrocarbon group, an aliphatic hydrocarbon group, or a heterocyclic group, each of which may have a substituent. Examples of the substituent may include: an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms. The aromatic hydrocarbon group as the substituent is an aryl group containing a monocycle or polycycle. The heterocyclic group as the substituent is, for example, a thienyl group, a furanyl group, a pyrrolyl group, an imidazolyl group, an oxazolyl group, a thiadiazolyl group, a pyrazolyl group, a pyridyl group, or a quinolyl group. $R_2$ and $R_3$ may each be an aryl group having a sulfonyl group.

$R_2$ and $R_3$ above are each independently preferably a thienyl group, a furanyl group, a pyrrolyl group, an imidazolyl group, an oxazolyl group, a thiadiazolyl group, a pyrazolyl group, a pyridyl group, or a quinolyl group, each of which may have a substituent, similarly to the case of the diazole derivative. This is because the fluorescent wavelength is shifted to the large wavelength side to obtain a larger stokes shift as compared with the case of using an unsubstituted group or a phenyl group. $R_2$ and $R_3$ each more preferably represent a thienyl group which may have a substituent, wherein the substituent is an aromatic hydrocarbon group, an aliphatic hydrocarbon group, or a heterocyclic group, each of which may have a substituent. As the substituent of the thienyl group, substituents similar to those in the case of the diazole derivative may be used.

Embodiment 2

A fluorescent dye according to this embodiment is a fluorescent dye including an imidazole derivative and may be represented by the following general formulae. Even if this imidazole derivative is used, an effect similar to that in the case of Embodiment 1 can be obtained.

[Chemical Formula 5]

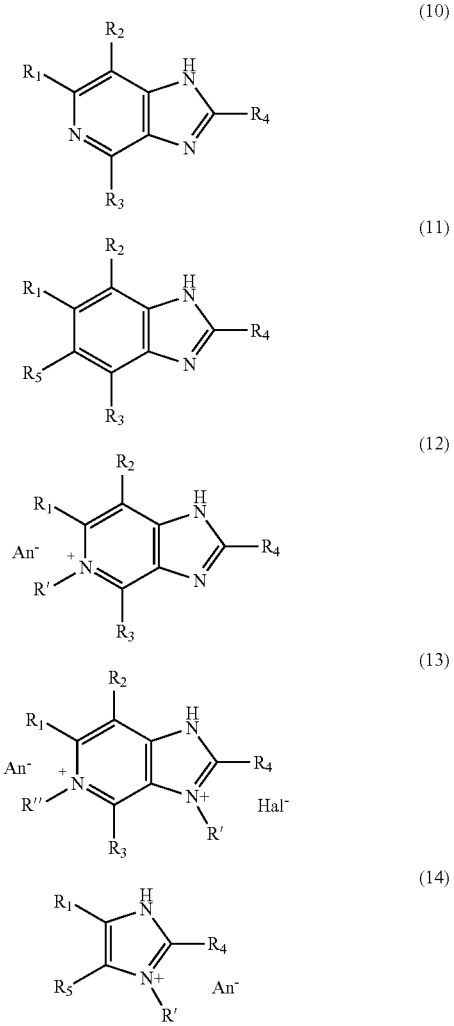

Here, one of $R_1$ and $R_4$ in the formulae (10), (12), and (13) and any one of $R_1$, $R_4$, and $R_5$ in the formulae (11) and (14) are each represented by the general formula $L_4$-$M_4$, wherein $M_4$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_4$ represents a linker which is represented by $-(CH=CR_6)_n-$ and which connects $M_4$ with a center pyridine ring or a center benzene ring, n represents an integer of from 1 to 5, $R_6$ represents any one of a hydrogen atom; a linear or branched alkyl group which may have a substituent and has 1 to 6 carbon atoms; a sulfo group which may have a substituent; a heterocyclic group selected from the group consisting of an imidazolium group, a pyridinium group, and a furan group, each of which may have a substituent; an amino group selected from the group consisting of a secondary amino group, a tertiary amino group, and a quaternary amino group, each of which may have a substituent; a hydroxy group which may have a substituent; an alkoxy group which may have a substituent; an aldehyde group which may have a substituent; a carboxyl group which may have a substituent; and an aromatic group which may have a substituent, the residues of $R_1$ and $R_4$ in the formulae (10), (12), and (13), the residues of $R_1$, $R_4$, and $R_5$ in the formulae (11) and (14), and $R_2$ and $R_3$ each independently represent a hydrogen atom, a halogen atom, or an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and An⁻ represents a halide ion, $CF_3SO_3^-$, $BF_4^-$, or $PF_6^-$.

$R_2$ and $R_3$ are each independently preferably an aromatic hydrocarbon group, an aliphatic hydrocarbon group, or a heterocyclic group, each of which may have a substituent. Examples of the substituent may include: an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms. The aromatic hydrocarbon group as the substituent is an aryl group containing a monocycle or polycycle. The heterocyclic group as the substituent is, for example, a thienyl group, a furanyl group, a pyrrolyl group, an imidazolyl group, an oxazolyl group, a thiadiazolyl group, a pyrazolyl group, a pyridyl group, or a quinolyl group. $R_2$ and $R_3$ may each be an aryl group having a sulfonyl group.

R' and R" each represent an aliphatic hydrocarbon group or an aromatic hydrocarbon group including an alkyl group which may have an aromatic ring. Here, as the aliphatic hydrocarbon group or the aromatic hydrocarbon group, ones similar to those described above may be used.

$R_2$ and $R_3$ above are each independently preferably a thienyl group, a furanyl group, a pyrrolyl group, an imidazolyl group, an oxazolyl group, a thiadiazolyl group, a pyrazolyl group, a pyridyl group, or a quinolyl group, each of which may have a substituent, similarly to the case of Embodiment 1. This is because the fluorescent wavelength is shifted to the large wavelength side to obtain a larger stokes shift as compared with the case of using an unsubstituted group or a phenyl group. $R_2$ and $R_3$ each more preferably represent a thienyl group which may have a substituent, wherein the substituent is an aromatic hydrocarbon group, an aliphatic hydrocarbon group, or a heterocyclic group, each of which may have a substituent. As the substituent of the thienyl group, substituents similar to those in the case of Embodiment 1 may be used.

Embodiment 3

A fluorescent dye according to this embodiment is a fluorescent dye including an azole derivative and may be represented by the following general formulae (4), (5), and (6).

[Chemical Formula 6]

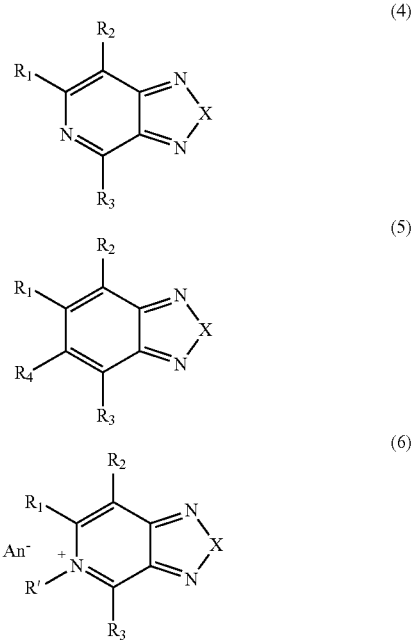

$R_1$ in the formulae (4) and (6) and one of $R_1$ and $R_4$ in the formula (5) are each represented by the general formula $L_2$-$M_2$, wherein $M_2$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_2$ represents a linker which connects $M_2$ with a center pyridine ring or a center benzene ring and which represents a direct bond or one or more types of functional groups selected from the group consisting of —$(CH_2)_n$— (n represents an integer of from 1 to 4), —NHCOO—, —CONH—, —COO—, —$SO_2$NH—, —HN—C(=NH)—NH—, —O—, —S—, —NR (R represents an alkyl group), —Ar— (Ar represents an aromatic hydrocarbon group), and —CO—Ar—NR—, the residues of $R_1$ and $R_4$ in the formula (5) and $R_2$ and $R_3$ in the formulae (4) to (6) each independently represent a thienyl group, a furanyl group, a pyrrolyl group, an imidazolyl group, an oxazolyl group, a thiadiazolyl group, a pyrazolyl group, a pyridyl group, or a quinolyl group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and An$^-$ represents a halide ion, $CF_3SO_3^-$, $BF_4^-$, or $PF_6^-$.

$R_2$ and $R_3$ each more preferably represent a thienyl group which may have a substituent, wherein the substituent is an aromatic hydrocarbon group, an aliphatic hydrocarbon group, or a heterocyclic group, each of which may have a substituent. Here, the aromatic hydrocarbon group which may have a substituent is an aryl group containing a monocycle or a polycycle, and specific examples of the aryl group may include a substituted or unsubstituted phenyl group, a naphthyl group, a biphenyl group and the like. In this case, the aromatic hydrocarbon group which may have a substituent may include the substituents in the number of 1 to 3. Examples of the substituents may include an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms.

Examples of the aliphatic hydrocarbon group which may have a substituent may include a substituted or unsubstituted, linear or branched alkyl group having 1 to 20 carbon atoms, an unsubstituted, linear or branched alkenyl group having 2 to 20 carbon atoms, and an unsubstituted, linear or branched alkynyl group having 2 to 20 carbon atoms and the like.

Examples of the heterocyclic group which may have a substituent may include substituted or unsubstituted furanyl group, pyrrolyl group, imidazolyl group, oxazolyl group, thiadiazolyl group, pyrazolyl group, pyridyl group, and quinolyl group. As the substituent of the thienyl group, an aromatic hydrocarbon group or an aliphatic hydrocarbon group which may have a substituent is preferable, and an aromatic hydrocarbon group which may have a substituent is more preferable, and specific examples may include substituted or unsubstituted phenyl group, naphthyl group, biphenyl group and the like. In this case, the aromatic hydrocarbon group which may have a substituent may include the substituents in the number of 1 to 3, and examples of the substituent may include an alkyl group, an alkenyl group, an alkynyl group, an alkoxy group, an alkyl ester group, a phosphate group, a sulfate group, a nitrile group, a hydroxyl group, a cyano group, a sulfonyl group, an aromatic hydrocarbon group, and a heterocyclic group. The alkyl group as the substituent is a substituted or unsubstituted, linear or branched alkyl group having 1 to 20 carbon atoms. The alkenyl group as the substituent is an unsubstituted, linear or branched alkenyl group having 2 to 20 carbon atoms. The alkynyl group as the substituent is an unsubstituted, linear or branched alkynyl group having 2 to 20 carbon atoms. The alkoxy group as the substituent is, for example, a methoxy group, an ethoxy group, a propoxy group, an isopropoxy group, a butoxy group, a pentyloxy group, or a phenoxy group. The alkyl ester group as the substituent is a linear or branched alkyl ester having 1 to 6 carbon atoms.

This embodiment also has an effect similar to that in the case of Embodiment 1. That is, the fluorescent dye has high water solubility, and therefore the rate of labeling for a biomolecule can be improved to thereby detect a biomolecule with high sensitivity. The excitation wavelength and emission wavelength are altered by changing the substituent to enable the use of two or more types of fluorescent dyes each having a large stokes shift, thereby making it possible to simultaneously detect a plurality of target molecules contained in one sample. When, particularly, a thienyl group which may have a substituent is used as $R_2$ and $R_3$, a stokes shift having more than 100 nm, preferably more than 120 nm, and more preferably more than 150 nm in a fluorescent wavelength of 600 nm or more is obtained, and therefore detection with high sensitivity can be performed without any influence of excitation light.

(Production Method)

The fluorescent dye of the present invention may be produced by the following method when, for example, a pyridyl group is contained as the nitrogen-containing group. That is a haloalkyl of an azole derivative or imidazole derivative is reacted with triphenylphosphine to prepare a phosphonium salt. Using this phosphonium salt and formyl pyridine, a pyridyl group is introduced through a double bond by Wittig reaction to obtain a pyridyl. When a pyridinium group is contained as the nitrogen cation-containing group, this pyridyl may be reacted with a bromo of an active ester to obtain a pyridinium salt, thereby producing the fluorescent dye of the present invention. Here, the haloalkyl may be obtained by using a method in which a halogenating agent is reacted with a hydroxy of an azole derivative or imidazole derivative. As the halogenating agent, thionyl chloride, phosphoryl chloride, phosphorous trichloride, phosphorous pentachloride, sulfuryl chloride, chlorine, thionyl bromide, bromine, or the like may be used. The halogenating agent is preferably thionyl chloride or phosphoryl chloride.

The description of the above method is to explain a method for obtaining a pyridinium salt containing an active ester which is to be a binding part mentioned below by using a bromo of an active ester in the case of the nitrogen cation-containing group. However, a pyridinium salt may also be produced by reacting pyridine introduced in the above manner with haloalkanes such as methyl iodide, haloalkenes, or halocarboxylic acids. In this case, when a functional group such as an isothiocyanate group or maleic acid anhydride which is to be a binding part mentioned below is contained at the terminal of these haloalkanes or haloalkenes, the pyridinium salt can be bonded to a biomolecule. When halocarboxylic acids are used, each of these acids is chemically bonded to pyridine to form a pyridinium having a carboxylic acid at its terminal, and therefore an active ester group such as hydroxysuccinimide can also be introduced.

The fluorescent dye of the present invention may be provided with a binding part that bonds to a biomolecule. For example, the nitrogen cation-containing group or nitrogen-containing group may be provided with a binding part. The binding part has a reactive group to be bonded to a biomolecules, and this reactive group is bonded with a biomolecule by a covalent bond or ionic bond.

When, for example, an amide bond, an imide bond, a urethane bond, an ester bond, or a guanidine bond is formed as the covalent bond, the reactive group is preferably a functional group which can be reacted with an amino group, imino group, thiol group, carboxyl group, or hydroxyl group of a biomolecule. For example, an isothiocyanate group, an isocyanate group, a maleic acid anhydride group, an epoxy group, a halogenated sulfonyl group, an acyl chloride group, an alkyl halide group, a glyoxal group, an aldehyde group, a triazine group, a carbodiimide group, an active-esterified carbonyl group or the like may be used as the functional group. It is preferable to use any one type selected from an isothiocyanate group, an isocyanate group, an epoxy group, a halogenated alkyl group, a triazine group, a carbodiimide group, and an active-esterified carbonyl group. It is more preferable to use any one type selected from an isothiocyanate group, an isocyanate group, an epoxy group, a halogenated alkyl group, a triazine group, a carbodiimide group, and an active-esterified carbonyl group. A triazine group, a carbodiimide group, or an active-esterified carbonyl group is even more preferable. For example, a carboxyl group may be used as the functional group of the nitrogen cation-containing group which is to be reacted with these reactive groups. For example, a N-hydroxysuccinimide ester or maleimide ester may also be used as the active-esterified carbonyl group. The fluorescent dye is bonded with a biomolecule by an amide bond through a N-hydroxy-succinimide ester by using N-hydroxy-succinimide and, as a condensation agent, N,N'-dicyclohexylcarbodiimide (DCC). As the carbodiimide group, a carbodiimide reagent such as DCC or 1-cyclohexyl-3-(2-morpholinoethyl)carbodiimide may be used. The fluorescent dye can be bonded with a biomolecule through the carbodiimide by an amide bond.

An anionic group and a cationic group can be used as the reactive group for forming the ionic bond. The anionic group such as sulfonyl group and carboxyl group can be used. These anionic groups can bond with a cationic group such as amino group and form the ionic bond. The nitrogen cation-containing group such as quaternary ammonium group and pyridinium group can be used as the cationic group. These cationic groups can bond with an anionic group such as carboxyl group and form the ionic bond. In the present invention, the nitrogen cation-containing group bonded with a center pyridine ring or a center benzene ring can also play a role of the cationic group as the reactive group.

(Application)

The fluorescent dye of the present invention can be applied to any method for detection of a biomolecule provided it is a method of measuring the fluorescence of a labeled biomolecule in solid or semi-solid state. By using an organic EL-dye instead of a conventional fluorescence dye, a detection method that provides high sensitivity, chemical stability and excellent handling property as well as low costs can be provided. In the present invention, the biomolecule sample can be labeled with a fluorescent dye by directly reacting the biomolecule sample with the fluorescent dye. Alternatively, a method for labeling a biomolecule sample with a fluorescent dye by reacting a biomolecule sample and a probe labeled with the fluorescent dye can be used. Furthermore, a method comprising size separating a biomolecule sample labeled with the fluorescent dye of the present invention by electrophoresis can be used. For example, the fluorescent dye of the present invention can be used in DNA microarray method for detecting nucleic acid and PCR method using such as a primer or terminator.

Where the object to be detected is a protein, a chromatic dye is used for the detection of the protein after electrophoresis. Generally, a method comprising penetrating a chromatic dye such as Coomassie Brilliant Blue (CBB) to a gel after electrophoresis to stain a protein and irradiating the protein with UV to cause luminescence is used. Although such method using a conventional chromatic dye is convenient, it is not suitable for the detection of trace protein because the sensitivity is low as about 100 ng. Furthermore, the method also has a problem in that long time is required for dying because the chromatic dye is penetrated through the gel. The fluorescent dye of the present invention is suitable for the detection of trace protein, because it has high sensitivity. Furthermore, the protein separated by size separation can also be identified by mass analysis.

Examples of the protein that can be detected include simple proteins such as albumin, globulin, glutelin, histone, protamine, collagen, etc., and conjugated proteins such as nucleus protein, glycoprotein, riboprotein, phosphoprotein, metal protein, etc. For example, phosphoprotein, glycoprotein and whole protein can be stained in a protein sample separated by two-dimensional electrophoresis using three organic fluorescent dyes that correspond to chromatic dyes for phosphoprotein, glycoprotein and whole protein. Furthermore, since the protein can be identified by mass analysis such as TOF-Mass, etc., it can be applied to the diagnosis or treatment of diseases that produce specific protein such as cancer, infectious diseases due to virus, etc. Collagen is a protein that constitutes binding tissues of animals, and has a unique fibrous structure, i.e., a structure having three polypeptide strands in which said peptide strands aggregate to form a triple strand. Generally, collagen is a protein having quite low immunogenicity, and is widely used in the fields of foods, cosmetics, pharmaceuticals, etc. However, where a fluorescence dye is introduced in the peptide strand of collagen, its stability is insufficient where a conventional fluorescence dye is used. Therefore, a more stable fluorescence dye is required. Accordingly, stable and high sensitivity detection can be carried out by using a fluorescent dye of the present invention for labeling collagen.

Further, a protein can be labeled by labeling an antibody specifically binding with a protein with a fluorescent dye of the present invention. For example, a fragment that referred to as $F(ab')_2$ can be obtained by treating an IgG antibody with pepsin. The fragment is reduced using dithiothreitol, etc. to give a fragment that referred to as Fab'. The Fab' fragment has one or two thiol group(s) (—SH). Specific reaction can be carried out by reacting the thiol group(s) with maleimide group(s). Namely, an antibody can be labeled with a fluorescent dye of the present invention by reacting the fluorescent dye in which maleimide group(s) have been introduced with thiol group(s) of a fragment. In this case, the physiological activity (antibody capturing ability) of the antibody is not deteriorated.

Meanwhile, a fluorescent dye of the present invention can be used for labeling an aptamer. Since the aptamer comprises an oligonucleic acid and can form various characteristic stereo structures depending on the base sequence, it can bind to many biomolecules including proteins via its stereo structure. Using this characteristic, the object substance can be detected by binding an aptamer labeled with the fluorescent dye of the present invention to a specific protein, and detecting indirectly the object substance to be detected from the variation of fluorescence according to the change of the structure of the protein due to binding to the object substance to be detected.

Alternatively, metal ion can be detected using a fluorescent dye of the present invention. Metal ion participates to every life phenomena that occur in a living body, such as maintenance of stability and high dimension structure of DNAs, proteins, etc. in a body, expression of functions, activation of enzymes that control all chemical reactions in a living body, etc. Therefore, importance of a metal ion sensor, which can observe behavior of metal ion in a living body in real time, is growing in the field of medical. Conventionally, a metal ion sensor in which a fluorescence dye has been introduced in a biomolecule is known. For example, a metal ion sensor that utilizes a nucleic acid having a sequence that forms a specific structure by incorporating $K^+$ ion in the presence of $K^+$ ion has been suggested (J. AM. CHEM. SOC. 2002, 124, 14286-14287). A fluorescence dye that initiates energy transfer is introduced in both ends of a nucleic acid. Generally, energy transfer does not occur due to distance between the dyes. However, in the presence of $K^+$ ion, the nucleic acid forms a specific shape, whereby the fluorescence dyes verge in a distance that occurs energy transfer and fluorescence can be observed. In addition, a zinc ion sensor in which a fluorescence dye has been introduced in a peptide has been suggested (J. Am. Chem. Soc. 1996, 118, 3053-3054). By using a label dye comprising a fluorescent dye of the present invention instead of these conventional fluorescence dyes, a metal ion sensor that provides high sensitivity and easy handling property can be provided. All kinds of metal ion existing in a living body can be detected.

Moreover, intercellular signal can be observed using a fluorescent dye of the present invention. For the response of cells to internal signal or environmental information, various molecules from ions to enzymes are participated. It is known that in the process of signal transmission, a specific protein kinase is activated and induces phosphoration of a specific cell protein, which bears initial response for various cell responses. Binding and hydrolysis of nucleotides play an important role in these activities, and signal transmission behavior can be readily observed using a nucleotide derivative. For example, protein kinase C (PKC) plays an important role for signal transmission in a cell membrane. This $Ca^{2+}$ dependant serine/threonine protein kinase is activated on a membrane-constituting lipid such as diacylglycerol, phosphatidyl serine, etc., which phosphorizes serine and threonine existing on an ion channel and a cell skeleton protein to vary electron charge on the membrane surface, whereby signal transmission is achieved. By dynamically observing these phenomena in living cells, signal transmission of the cells can be observed.

In this observation, the nucleotide derivative is provided as a substrate or an inhibitor for an enzyme, and it is used for search for the structure and dynamics of a lone protein and reconstruction of a membrane binding protein enzyme, and binds to organelle such as mitochondria, nucleotide-binding protein portion of tissues such as skinned muscle fiber so as to control them. Furthermore, existence of compounds that affect signal transmission such as inhibitors or active forms for G-protein has been recently revealed. By introducing the labeled dye including the organic EL-dye of the present invention into this nucleotide derivative, dynamic observation of the intercellular signal transmission thereof can be carried out at high sensitivity and with easy handling.

The fluorescent dye of the present invention can also be used as a chromatic dye for tissues or cells used for determination of the expression level of the target nucleic acid or target protein in a tissue sample or a cell sample. The tissues or cells can be stained by binding the fluorescent dye of the present invention with a target nucleic acid or a target protein via reactive groups as mentioned above.

Accordingly, the fluorescent dye of the present invention shows superior performance than conventional dyes in view of storage after labeling. Furthermore, it can also be sufficiently used as a dye for cell skeletons as well as a dye for eucaryotic cells. Moreover, it can be used for labeling of mitochondria, Golgi body, endoplasmic reticulumlysosome, lipid double membrane, etc. These labeled cells, etc. can be observed under all wet or dry conditions, and thus have great versatility. A fluorescence microscope, etc. can be used for observation.

Tissues collected from a human body in a clinical stage are each sliced into a thin film by using an instrument such as a microtome, and is then dyed. Here, a Cy dye and Alexa dye are used. However, the existing dyes are very unstable, and it is therefore necessary to produce a sample again in rediagnosis. The sample produced cannot be preserved as a specimen. However, the fluorescent dye of the present invention is very stable as compared with the above existing dyes, and therefore tissues dyed can be preserved as a specimen.

Also, an immunoassay utilizing the specific recognition performance of an antibody is used for the diagnosis of cancers, infectious diseases and the like. This immunoassay is a method of detecting an objective antigen by using a labeled antibody, and, for example, an enzyme immunoassay (ELISA method) using an enzyme as a labeled substance and a fluorescent immunoassay (FIA method) using a fluorescent dye as a labeled substance are used. In the ELISA method, final detection is attained by detecting and quantitatively measuring various signals (for example, color development, luminescence, and chemiluminescence) generated by the reaction of an enzyme serving as a labeled substance. The FIA method is, on the other hand, performed by irradiating a fluorescent dye serving as a labeled substance with excitation light to thereby detect and quantitatively measure the fluorescent light resulted from the irradiation. Since the FIA method uses a fluorescent dye, the method has the characteristics that it provides a clear contrast and excellent quantitativity, and also enables detection in a shorter time, and is performed by simple operation as compared with the ELISA method. However, a conventional fluorescent dye has a problem concerning a low labeling rate. For example, though a fluorescent dye is used in a molar amount of about 200 times based on an antibody, the rate of labeling is about 50 to 60% even in this condition. For this reason, it is necessary to use a fluorescent dye in a large amount, and therefore there is a problem concerning high detection cost and also requiring a long time for detection because of the necessity of a process for removing an unreacted fluorescent dye. Contrary to this, the use of the fluorescent dye of the present invention can increase the rate of labeling, enabling highly sensitive detection.

The fluorescent dye of the present invention may also be used for cosmetic compositions. The cosmetic compositions containing a fluorescent dye are used not only for performance cosmetics at night and in a room, but also for foundations, hair dyes, and the like by utilizing the color-brightening effect of the fluorescent dye. Here, the color-brightening effect refers to the effect that a fluorescent dye absorbs ultraviolet light and emits visible light to impart brightness and vividness to the skin and hair. Although fluorescent lamps emitting daylight color or white light are used for indoor lighting in Japan, these fluorescent lamps mainly emit blue or green light but few red light. For this reason, there is the problem that the makeup skin of female looks pale and dark. Contrary to this, a vividly reddish color can be developed to solve the dark-color problem by using the fluorescent dye of the present invention which emits, for example, orange light. When the fluorescent dye of the present invention is used for hair dyeing, it can not only change the color of hair by rays emitted in a visible region, but also increase the brightness of hair.

The fluorescent dye of the present invention may also be used for marking agents. Although the marking agent containing the fluorescent dye of the present invention is invisible under normal visible light, it allows the fluorescent dye to emit light by irradiating it with excitation light such as ultraviolet rays, thereby enabling visual recognition. This marking agent may be used for the discrimination of, for example, products and human bodies and for the detection of substances for the purpose of crime prevention or criminal investigation by utilizing this nature. The objects of the marking agent include products and human bodies which are the objects of prevention of crimes such as forgeries and robberies or criminal investigation. Examples of these products and human bodies may include paper money, checks, stocks, important documents such as various certificates, products such as an automobile, a motorcycle, a bicycle, a work of art, furniture, brand items, and clothes, body surface parts such as human skin, hair, and nail, materials left behind such as latent fingerprints, and the like. Further, examples of the material constituting the objects may include paper such as wood free paper, OCR paper, non-carbon paper, and art paper, plastics such as vinyl chloride, polyester, polyethylene terephthalate, and polypropylene, metals, glasses, ceramics, natural fibers such as wool, cotton, silk, and hemp, synthetic fibers such as a regenerated cellulose fiber, a polyvinyl alcohol fiber, a polyamide fiber, and a polyester fiber, proteins in the human skin and body fluid, and the like.

EXAMPLES

The present invention will be described in more detail by way of working examples, but the scope of the present invention is not limited by the following working examples.

Synthetic Example 1

An example of synthesis of a nitrogen cation of 4,7-diphenyl-1,2,5-oxadiazolopyridine will be shown below.

Scheme 1

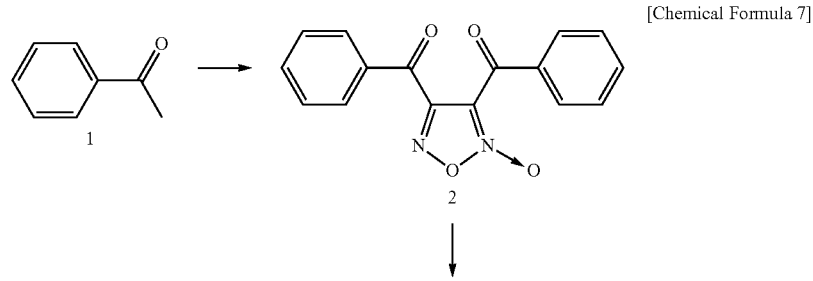

[Chemical Formula 7]

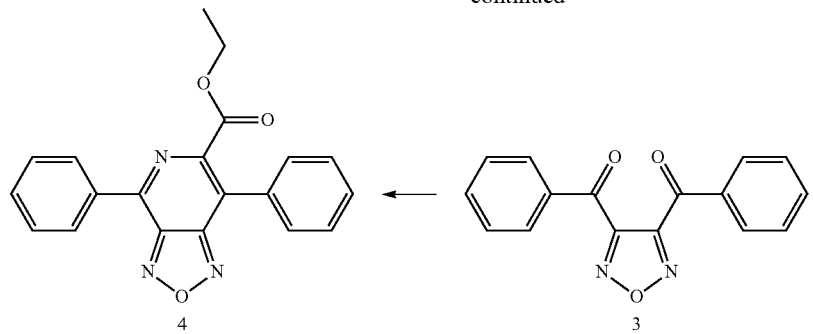

(1) Synthesis of a Diketone Derivative (2)

In a 500 ml three-neck flask, 30.0 g (0.25 mol) of 4-methoxyacetophenone (1) and 0.15 g of sodium nitrite were dissolved in 100 ml of acetic acid. A solution prepared by dissolving 100 ml of nitric acid in 100 ml of acetic acid was added dropwise to the solution in a water bath over 1 hour. Then, the obtained solution was stirred at room temperature for 2 days. The reaction mixture was gradually poured into 500 ml of water to produce a precipitate. The precipitate was filtrated and dissolved in chloroform. The chloroform phase was washed with saturated sodium bicarbonate water, and also washed twice with an aqueous 10% NaCl solution. The washed precipitate was dehydrated over magnesium sulfate anhydride, and then chloroform was distilled off under reduced pressure to obtain oxadiazole-N-oxide (2) (yield amount: 30.5 g, yield: 82%).

(2) Synthesis of a Diketone Derivative (3)

In a 500 ml three-neck flask, 14.7 g (0.05 mol) of the oxadiazole-N-oxide (2) was dissolved in 400 ml of acetonitrile. To this, 6.0 g of metal zinc, 7 ml of acetic acid, and 20 ml of acetic acid anhydride were added. The obtained solution was cooled in a water bath so that the reaction temperature did not exceed 35° C. The mixture was stirred for 6 hours to terminate the reaction. The reaction mixture was filtrated to remove insoluble matters. Acetonitrile was distilled off under reduced pressure to obtain a residue. The residue was recrystallized from chloroform to obtain an oxadiazole dibenzoyl (3) (yield amount: 9.6 g, yield: 69%).

(3) Synthesis of a Diphenyloxadiazolopyridine Ethyl Ester

In a 500 ml three-neck flask, 10.0 g (0.035 mol) of the oxadiazole dibenzoyl (3) was dissolved in 300 ml of butanol. To this, 32.0 g (0.23 mol) of glycine ethyl ester hydrochloride was added. The obtained mixture was refluxed under heating for 24 hours. Butanol was distilled off under reduced pressure to obtain a residue. The residue was dissolved in 200 ml of chloroform and washed with 10% hydrochloric acid, then with saturated sodium bicarbonate water, and with an aqueous 10% NaCl solution. The washed residue was dried over magnesium sulfate anhydride to remove the solvent. The obtained residue was recrystallized from chloroform to obtain a 4,7-diphenyl-1,2,5-oxadiazolopyridine ethyl ester (4) (hereinafter referred to as an ester (4)) (yield amount: 7.6 g, yield: 65%).

Then, the ester (4) was subjected to a reducing reaction in the presence of $NaBH_4$ to obtain a diamino alcohol (5). The obtained alcohol (5) was reacted with thionyl chloride to obtain a thiadiazolopyridine chloromethyl (6). The obtained thiadiazolopyridine chloromethyl (6) was reacted with triphenylphosphine to obtain a phosphonium salt (7), which was then subjected to a Wittig reaction to obtain a vinyl (8) so that a pyridinium salt (9) (in the case where L is —CH=CH—) containing an active ester was synthesized. An example of the reaction is shown below.

Scheme 2

[Chemical Formula 8]

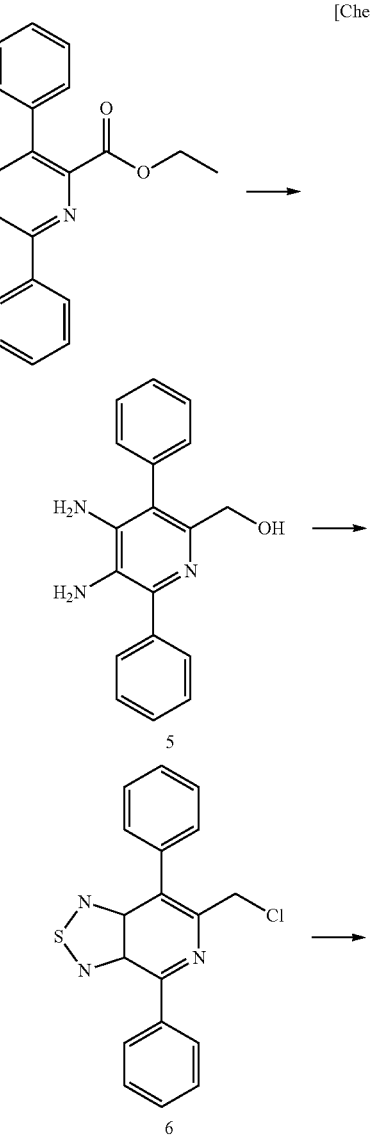

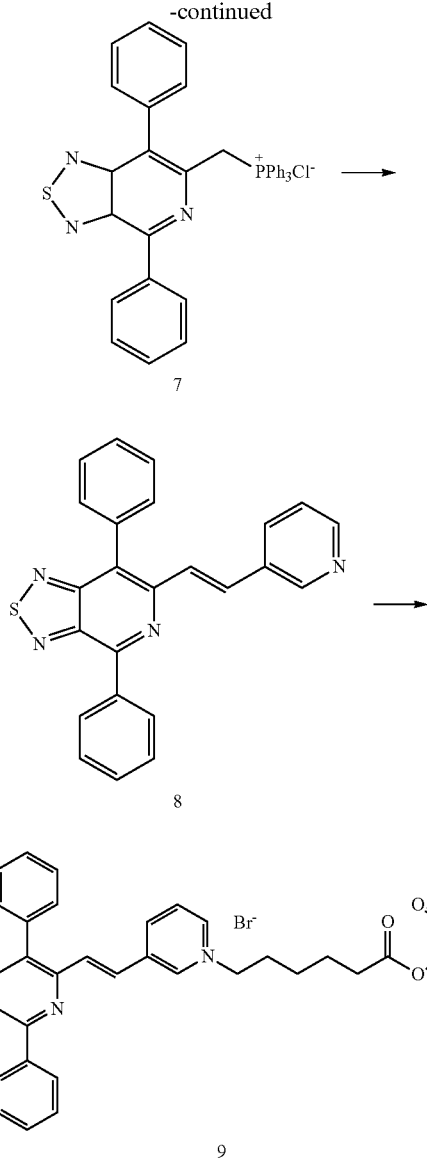

(4) Synthesis of a Diamino Alcohol (5)

A solution (100 ml) of the ester (4) (1.73 g, 5 mmol) and NaBH₄ (1.30 g, 35 mmol) in ethanol was refluxed under heating for 12 hours. Then, the reaction solution was poured into water, which was allowed to stand overnight. Then, the precipitate was filtrated to obtain a diamino alcohol (5) (yield amount: 1.17 g yield: 80%).

(5) Synthesis of a Chloromethyl (6)

Thionyl chloride (6 ml) and pyridine-NaBH₄ (3 ml) were added dropwise in this order to a solution (60 ml) of the alcohol (5) (1.17 g) in chloroform, and the mixture was refluxed under heating for 3 hours and 30 minutes. Then, the reaction solution was poured into water, which was neutralized with saturated sodium bicarbonate water and extracted with chloroform. The extract was dried over magnesium sulfate anhydride and the residue obtained after distillation under reduced pressure was subjected to column treatment (Kanto C-60, Hexane/Chloroform=3/1 (v/v)) to obtain a chloromethyl (6) (yield amount: 1.11 g, yield: 82%).

(6) Synthesis of a Phosphonium Salt (7)

A solution (5 ml) of 112.6 mg (0.33 mmol) of the chloromethyl (6) and triphenylphosphine (96 mg, 0.37 mmol) in toluene was refluxed under heating for 3 days, and the precipitate was filtrated and washed with ether to obtain a phosphonium salt (7) (yield amount: 108 mg, yield: 55%).

(7) Synthesis of a Vinyl (8)

The phosphonium salt (7) (140.5 mg, 0.23 mmol) was added to a solution (1 ml) of m-formylpyridine (16 μL, 0.18 mmol) and potassium hydroxide (purity: 85%, 15 mg) in ethanol under ice-cooling, and the mixture was stirred at the temperature for 1 hour and 30 minutes. The precipitate was filtrated and washed with ethanol and then with water, followed by drying to obtain 4,7-diphenyl-1,2,5-oxadiazolopyridine-6-(4-vinylpyridine) (hereinafter referred to as a vinyl (8)) (yield amount: 44 mg, yield: 62%).

(8) Synthesis of a Pyridinium Salt (9) Containing an Active Ester

A solution (2 ml) of the vinyl (8) (40 mg, 0.10 mmol) and a bromohexanoic acid active ester (32 mg, 0.11 mol) in toluene was refluxed under heating for 5 days, and then the precipitate was filtrated to obtain a pyridinium salt (9) containing an active ester.

Synthetic Example 2

An example of synthesis of a nitrogen cation of 4,7-di(methoxyphenyl)-1,2,5-oxadiazolopyridine will be shown below.

Scheme 3

[Chemical Formula 9]

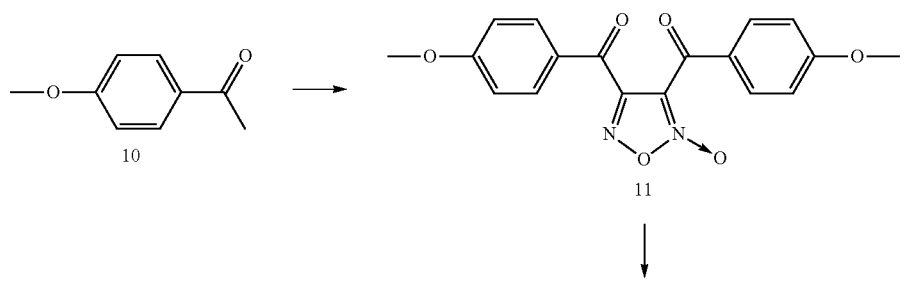

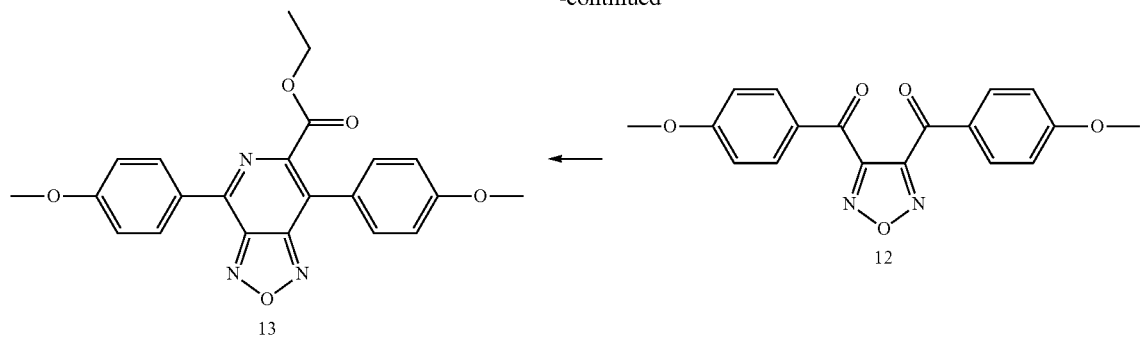

(1) Synthesis of a Diketone Derivative (11)

in a 500 ml three-neck flask, 37.5 g (0.25 mol) of 4-methoxyacetophenone (10) and 0.15 g of sodium nitrite were dissolved in 100 ml of acetic acid. A solution prepared by dissolving 100 ml of nitric acid in 100 ml of acetic acid was added dropwise to the solution in a water bath over 2 hours. Then, the obtained solution was stirred at room temperature for 2 days. The reaction mixture was gradually poured into 500 ml of water to produce a precipitate. The precipitate was filtrated and dissolved in chloroform. The chloroform phase was washed with saturated sodium bicarbonate water, and also washed twice with an aqueous 10% NaCl solution. The washed precipitate was dehydrated over magnesium sulfate anhydride, and then chloroform was distilled off under reduced pressure to obtain oxadiazole-N-oxide (11) (yield amount: 34.5 g, yield: 78%).

(2) Synthesis of a Diketone Derivative (12)

In a 500 ml three-neck flask, 17.7 g (0.05 mol) of the oxadiazole-N-oxide (11) was dissolved in 400 ml of acetonitrile. To this, 12.0 g of metal zinc, 7 ml of acetic acid, and 20 ml of acetic acid anhydride were added. The obtained solution was cooled in a water bath so that the reaction temperature did not exceed 30° C. The mixture was stirred for 12 hours to terminate the reaction. The reaction mixture was filtrated to remove insoluble matters. Acetonitrile was distilled off under reduced pressure to obtain a residue. The residue was recrystallized from chloroform to obtain oxadiazole-N-oxide (12) (yield amount: 10.2 g, yield: 60%).

(3) Synthesis of a Dimethoxyphenyloxadiazolopyridine Ethyl Ester (13)

In a 500 ml three-neck flask, 15.6 g (0.046 mol) of the oxadiazole-N-oxide (12) was dissolved in 300 ml of butanol. To this, 32.0 g (0.23 mol) of glycine ethyl ester hydrochloride was added. The obtained mixture was refluxed under heating for 24 hours. Butanol was distilled off under reduced pressure to obtain a residue. The residue was dissolved in 200 ml of chloroform and washed with 10% hydrochloric acid, then with saturated sodium bicarbonate water, and with an aqueous 10% NaCl solution. The washed residue was dried over magnesium sulfate anhydride to remove the solvent. The obtained residue was recrystallized from chloroform to obtain a 4,7-di(methoxyphenyl)-1,2,5-oxadiazolopyridine ethyl ester (13) (hereinafter referred to as an ester (13)) (yield amount: 13.0 g, yield: 70%).

Then, the ester (13) was subjected to a reducing reaction in the presence of NaBH$_4$ to obtain a hydroxymethyl (14). The obtained hydroxymethyl (14) was reacted with thionyl chloride to obtain an oxadiazolopyridine chloromethyl (15). The obtained oxadiazolopyridine chloromethyl (15) was reacted with triphenylphosphine to obtain a phosphonium salt (16), which was then subjected to a Wittig reaction to synthesize a pyridinium salt (18) (in the case where L is —CH=CH—) containing an active ester. An example of the reaction is shown below.

Scheme 4

[Chemical Formula 10]

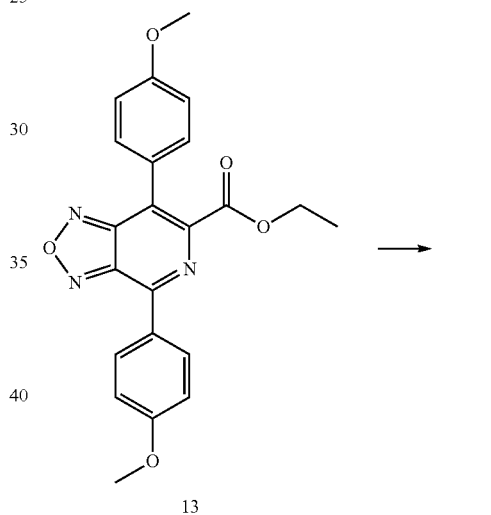

13

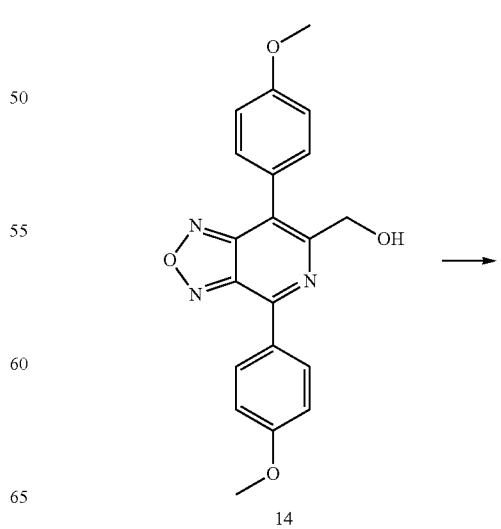

14

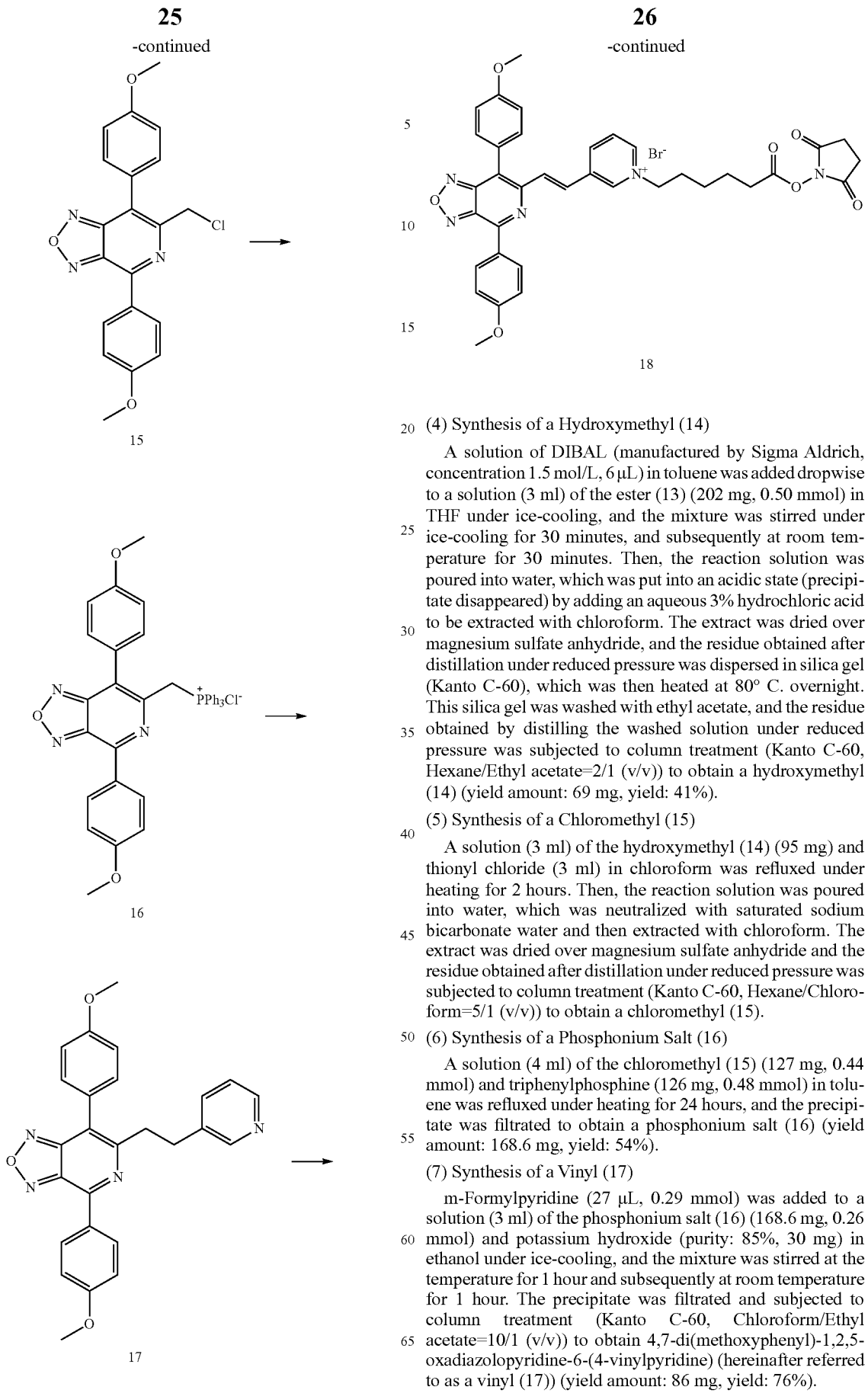

(4) Synthesis of a Hydroxymethyl (14)

A solution of DIBAL (manufactured by Sigma Aldrich, concentration 1.5 mol/L, 6 μL) in toluene was added dropwise to a solution (3 ml) of the ester (13) (202 mg, 0.50 mmol) in THF under ice-cooling, and the mixture was stirred under ice-cooling for 30 minutes, and subsequently at room temperature for 30 minutes. Then, the reaction solution was poured into water, which was put into an acidic state (precipitate disappeared) by adding an aqueous 3% hydrochloric acid to be extracted with chloroform. The extract was dried over magnesium sulfate anhydride, and the residue obtained after distillation under reduced pressure was dispersed in silica gel (Kanto C-60), which was then heated at 80° C. overnight. This silica gel was washed with ethyl acetate, and the residue obtained by distilling the washed solution under reduced pressure was subjected to column treatment (Kanto C-60, Hexane/Ethyl acetate=2/1 (v/v)) to obtain a hydroxymethyl (14) (yield amount: 69 mg, yield: 41%).

(5) Synthesis of a Chloromethyl (15)

A solution (3 ml) of the hydroxymethyl (14) (95 mg) and thionyl chloride (3 ml) in chloroform was refluxed under heating for 2 hours. Then, the reaction solution was poured into water, which was neutralized with saturated sodium bicarbonate water and then extracted with chloroform. The extract was dried over magnesium sulfate anhydride and the residue obtained after distillation under reduced pressure was subjected to column treatment (Kanto C-60, Hexane/Chloroform=5/1 (v/v)) to obtain a chloromethyl (15).

(6) Synthesis of a Phosphonium Salt (16)

A solution (4 ml) of the chloromethyl (15) (127 mg, 0.44 mmol) and triphenylphosphine (126 mg, 0.48 mmol) in toluene was refluxed under heating for 24 hours, and the precipitate was filtrated to obtain a phosphonium salt (16) (yield amount: 168.6 mg, yield: 54%).

(7) Synthesis of a Vinyl (17)

m-Formylpyridine (27 μL, 0.29 mmol) was added to a solution (3 ml) of the phosphonium salt (16) (168.6 mg, 0.26 mmol) and potassium hydroxide (purity: 85%, 30 mg) in ethanol under ice-cooling, and the mixture was stirred at the temperature for 1 hour and subsequently at room temperature for 1 hour. The precipitate was filtrated and subjected to column treatment (Kanto C-60, Chloroform/Ethyl acetate=10/1 (v/v)) to obtain 4,7-di(methoxyphenyl)-1,2,5-oxadiazolopyridine-6-(4-vinylpyridine) (hereinafter referred to as a vinyl (17)) (yield amount: 86 mg, yield: 76%).

(8) Synthesis of a Pyridinium Salt (18) Containing an Active Ester

A solution (2 ml) of the vinyl (17) (86 mg, 0.20 mmol) and a bromohexanoic acid active ester (63 mg, 0.22 mol) in toluene was refluxed under heating for 3 days, and then the precipitate was filtrated to obtain a pyridinium salt (18) containing an active ester.

Synthetic Example 3

An example of synthesis of a nitrogen cation of 4,7-diphenyl-1,2,5-thiadiazolopyridine will be shown below.

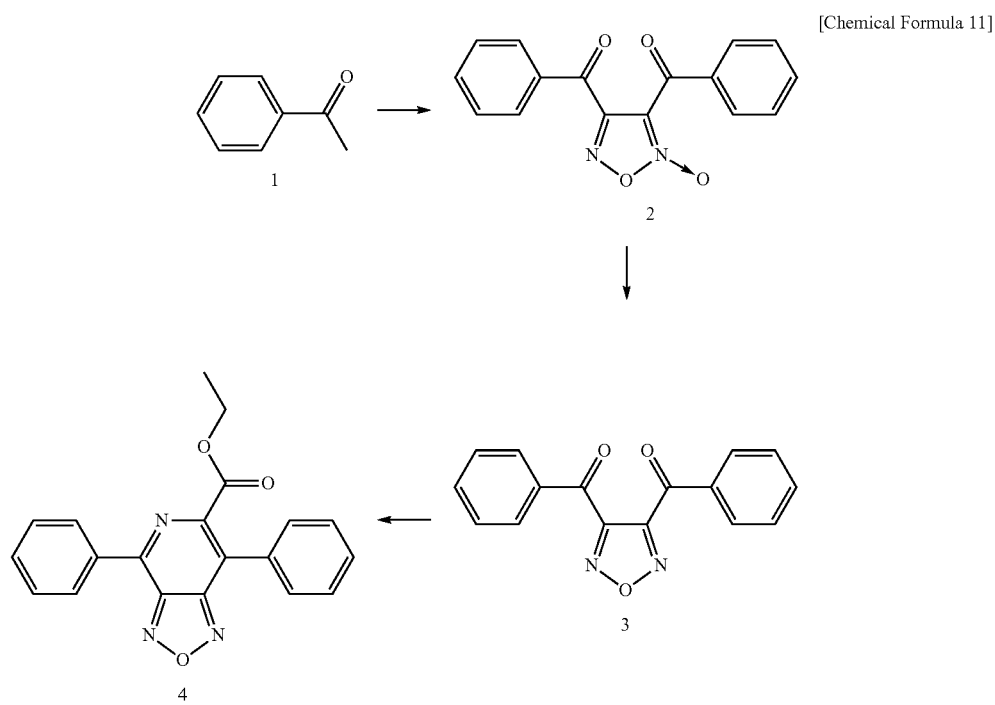

(1) Synthesis of a Diketone Derivative (2)

In a 500 ml three-neck flask, 30.0 g (0.25 mol) of 4-methoxyacetophenone (1) and 0.15 g of sodium nitrite were dissolved in 100 ml of acetic acid. A solution prepared by dissolving 100 ml of nitric acid in 100 ml of acetic acid was added dropwise to the solution in a water bath over 1 hour. Then, the obtained solution was stirred at room temperature for 2 days. The reaction mixture was gradually poured into 500 ml of water to produce a precipitate. The precipitate was filtrated and dissolved in chloroform. The chloroform phase was washed with saturated sodium bicarbonate water, and also washed twice with an aqueous 10% NaCl solution. The washed precipitate was dehydrated over magnesium sulfate anhydride, and then chloroform was distilled off under reduced pressure to obtain oxadiazole-N-oxide (2) (yield amount: 30.5 g, yield: 82%).

(2) Synthesis of a Diketone Derivative (3)

In a 500 ml three-neck flask, 14.7 g (0.05 mol) of the oxadiazole-N-oxide (2) was dissolved in 400 ml of acetonitrile. To this, 6.0 g of metal zinc, 7 ml of acetic acid, and 20 ml of acetone were added. The obtained solution was cooled in a water bath so that the reaction temperature did not exceed 35° C. The mixture was stirred for 6 hours to terminate the reaction. The reaction mixture was filtrated to remove insoluble matters. Acetonitrile was distilled off under reduced pressure to obtain a residue. The residue was recrystallized from chloroform to obtain an oxadiazole dibenzoyl (3) (yield amount: 9.6 g, yield: 69%).

(3) Synthesis of Diphenyloxadiazolopyridine Ethyl Ester (4)

In a 500 ml three-neck flask, 10.0 g (0.035 mol) of the oxadiazole dibenzoyl (3) was dissolved in 300 ml of butanol. To this, 32.0 g (0.23 mol) of glycine ethyl ester hydrochloride was added. The obtained mixture was refluxed under heating for 24 hours. Butanol was distilled off under reduced pressure to obtain a residue. The residue was dissolved in 200 ml of chloroform and washed with 10% hydrochloric acid, then with saturated sodium bicarbonate, and with an aqueous 10% NaCl solution. The washed residue was dried over magnesium sulfate anhydride to remove the solvent. The obtained residue was recrystallized from chloroform to obtain a 4,7-diphenyl-1,2,5-oxadiazolopyridine ethyl ester (4) (hereinafter referred to an ester (4)) (yield amount: 7.6 g, yield: 65%).

Then, the ester (4) was subjected to a reducing reaction in the presence of $NaBH_4$ to obtain a diamino alcohol (5). The obtained alcohol (5) was reacted with thionyl chloride to obtain a thiadiazolopyridine chloromethyl (6). The obtained thiadiazolopyridine chloromethyl (6) was reacted with triphenylphosphine to obtain a phosphonium salt (7), which was then subjected to a Wittig reaction to obtain a vinyl so that a pyridinium salt (in the case where L is —CH=CH—) containing an active ester was synthesized. An example of the reaction is shown below.

Scheme 6

[Chemical Formula 12]

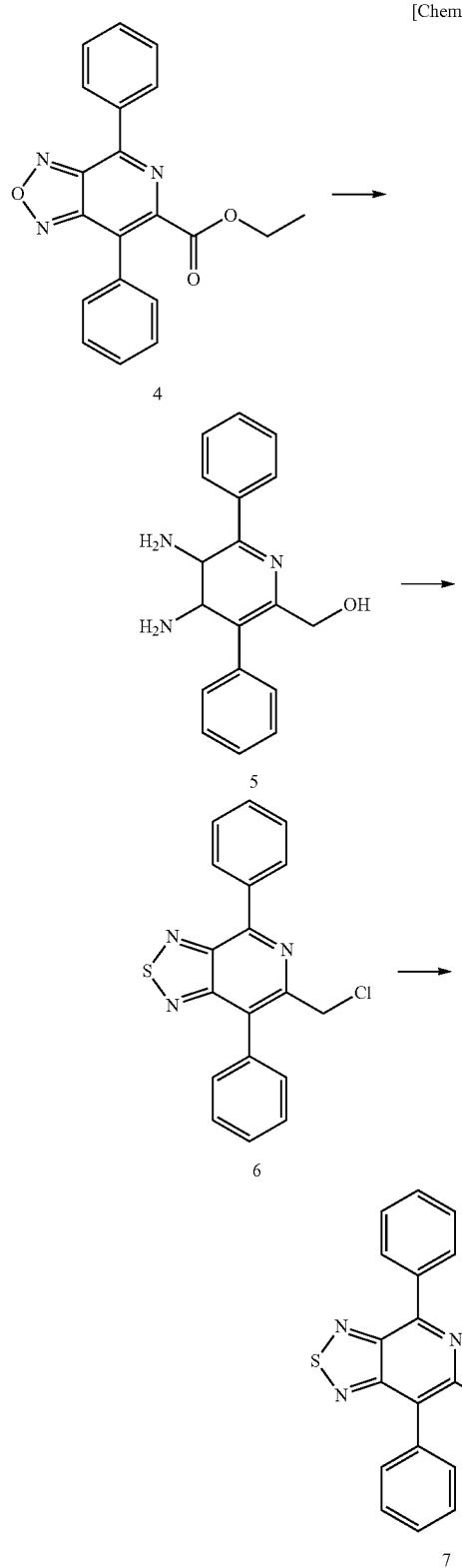

heating for 12 hours. Then, the reaction solution was poured into water, which was allowed to stand overnight. Then, the precipitate was filtrated to obtain a diamino alcohol (5) (yield amount: 1.17 g, yield: 80%).

(5) Synthesis of a Chloromethyl (6)

Thionyl chloride (6 ml) and pyridine-$NaBH_4$ (3 ml) were added dropwise in this order to a solution (60 ml) of the alcohol (5) (1.17 g) in chloroform, and the mixture was refluxed under heating for 3 hours and 30 minutes. Then, the reaction solution was poured into water, which was neutralized with saturated sodium bicarbonate and extracted with chloroform. The extract was dried over magnesium sulfate anhydride and the residue obtained after distillation under reduced pressure was subjected to treatment using a column chromatography (Kanto C-60, Hexane/Chloroform=3/1 (v/v)) to obtain a chloromethyl (6) (yield amount: 1.11 g, yield: 82%).

(6) Synthesis of a Phosphonium Salt (7)

A solution (5 ml) of 112.6 mg (0.33 mmol) of the chloromethyl (6) and triphenylphosphine (96 mg, 0.37 mmol) in toluene was refluxed under heating for 3 days, and the precipitate was filtrated and washed with ether to obtain a phosphonium salt (7) (yield amount: 108 mg, yield: 55%).

Scheme 7

[Chemica Formula 13]

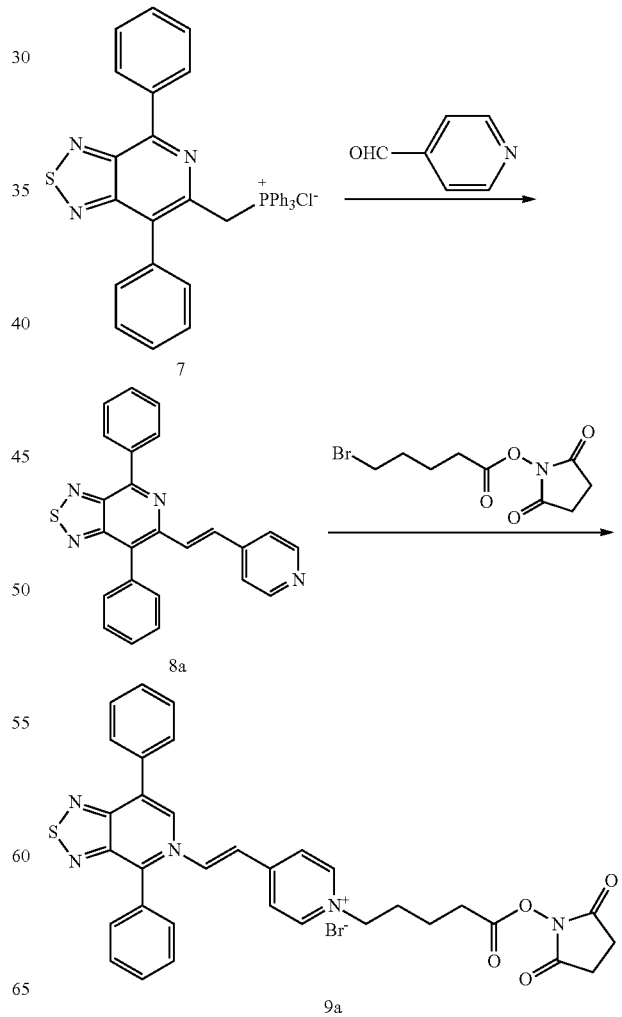

(4) Synthesis of a Diamino Alcohol (5)

A solution (100 ml) of 1.73 g (5 mmol) of the ester (4) and 1.30 g (35 mmol) of $NaBH_4$ in ethanol was refluxed under (7) Synthesis of a Vinyl (8a)

p-Formylpyridine (27 μL, 0.29 mmol) was added to a solution (3 ml) of the phosphonium salt (7) (168.6 mg. 0.26 mmol) and potassium hydroxide (purity: 85%, 30 mg) in ethanol under ice-cooling, and the mixture was stirred at the temperature for 1 hour and then at room temperature for 1 hour. The precipitate was filtrated and subjected to column treatment to obtain 4,7-diphenyl-1,2,5-oxadiazolopyridine-6-(4-vinylpyridine) (hereinafter referred to as a vinyl (8a)) (yield amount: 67 mg, yield: 66%).

(8) Synthesis of a Pyridinium Salt (9a) Containing an Active Ester

A solution (4 ml) of the vinyl (8a) (63 mg, 0.16 mmol) and a bromohexanoic acid active ester (50 mg, 0.18 mol) in toluene was refluxed under heating for 3 days, and then the precipitate was filtrated to obtain a 4-vinylpyridinium salt (9a) containing an active ester.

Synthetic Example 4

A 3-vinylpyridinium salt containing an active ester was synthesized by using, as a starting material, the phosphonium salt (7) synthesized in Synthetic Example 3. An example of synthesis will be shown below.

Scheme 8

[Chemical Formula 14]

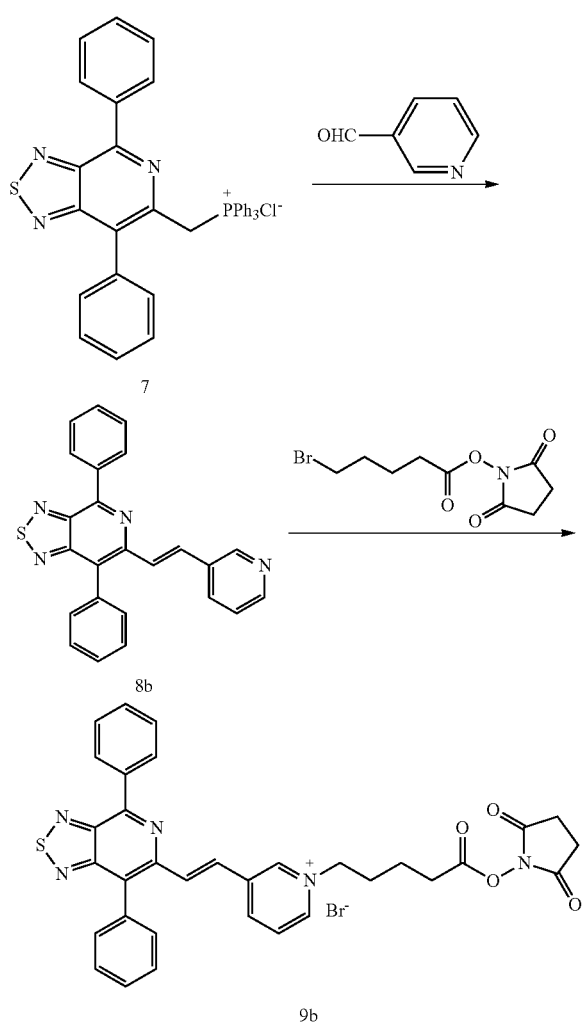

(1) Synthesis of a Vinyl (8b)

m-Formylpyridine (26 μL, 0.28 mmol) was added to a solution (4 ml) of the phosphonium salt (7) (150 mg, 0.25 mmol) and potassium hydroxide (purity: 85%, 30 mg) in ethanol under ice-cooling, and the mixture was stirred at the temperature for 1 hour and then at room temperature for 1 hour. The precipitate was filtrated and subjected to column treatment to obtain 4,7-diphenyl-1,2,5-oxadiazolopyridine-6-(3-vinylpyridine) (hereinafter referred to as a vinyl (8b)) (yield amount: 57 mg, yield: 58%).

(2) Synthesis of a Pyridinium Salt (9b) Containing an Active Ester

A solution (4 ml) of the vinyl (8a) (40 mg, 0.10 mmol) and a bromohexanoic acid active ester (31 mg, 0.11 mol) in toluene was refluxed under heating for 4 days, and then the precipitate was filtrated to obtain a 3-vinylpyridinium salt (9a) containing an active ester.

Synthetic Example 5

A 2-vinylpyridinium salt containing an active ester was synthesized by using, as a starting material, the phosphonium salt (7) synthesized in Synthetic Example 3. An example of synthesis will be shown below.

Scheme 9

[Chemica Formula 15]

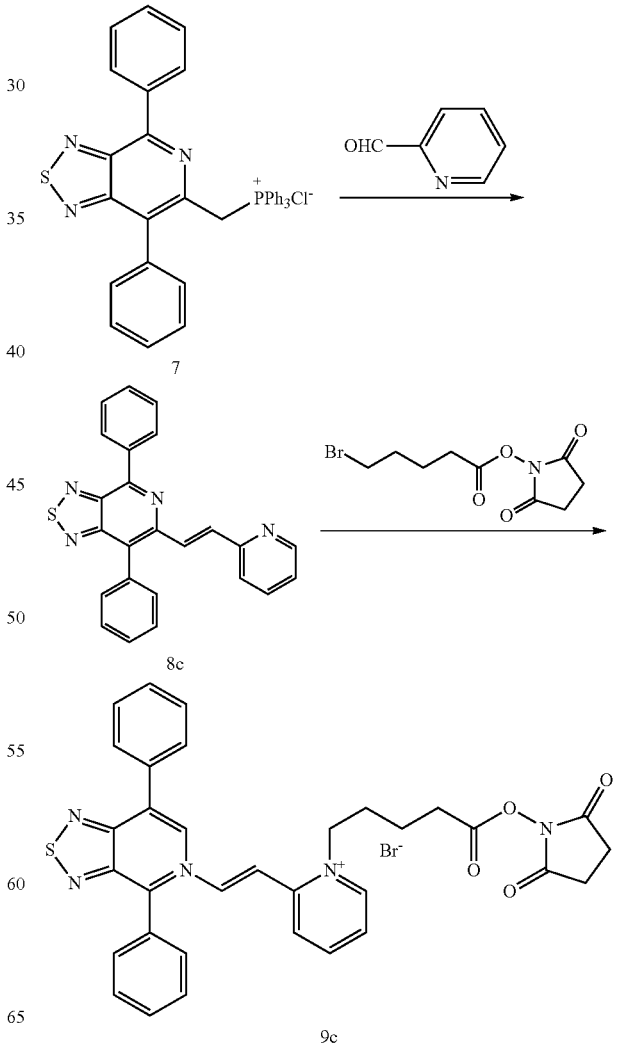

(1) Synthesis of a Vinyl (8c)

o-Formylpyridine (17 µL, 0.19 mmol) was added to a solution (4 ml) of the phosphonium salt (7) (100 mg, 0.17 mmol) and potassium hydroxide (purity: 85%, 30 mg) in ethanol under ice-cooling, and the mixture was stirred at the temperature for 1 hour and then at room temperature for 1 hour. The precipitate was filtrated and subjected to column treatment to obtain 4,7-diphenyl-1,2,5-thiadiazolopyridine-6-(2-vinylpyridine) (hereinafter referred to as a vinyl (8c)) (yield amount: 49 mg, yield: 73%).

(2) Synthesis of a Pyridinium Salt (9c) Containing an Active Ester

A solution (3 ml) of the vinyl (8c) (40 mg, 0.10 mmol) and a bromohexanoic acid active ester (31 mg, 0.11 mol) in toluene was refluxed under heating for 3 days, and then the precipitate was filtrated to obtain a 2-vinylpyridinium salt (9c) containing an active ester.

Synthetic Example 6

An example of synthesis of a nitrogen cation of 4,7-di(methylphenyl)-1,2,5-thiadiazolopyridine will be shown below.

(2) Synthesis of a Diketone Derivative (12)

In a 500 ml three-neck flask, 15.0 g (0.05 mol) of the oxadiazole-N-oxide (11) was dissolved in 400 ml of acetonitrile. To this, 6.0 g of metal zinc, 7 ml of acetic acid, and 20 ml of acetone were added. The obtained solution was cooled in a water bath so that the reaction temperature did not exceed 35° C. The mixture was stirred for 6 hours to terminate the reaction. The reaction mixture was filtrated to remove insoluble matters. Acetonitrile was distilled off under reduced pressure to obtain a residue. The residue was recrystallized from chloroform to obtain an oxadiazole dibenzoyl (12) (yield amount: 8.4 g, yield: 59%).

(3) Synthesis of a Dimethylphenyloxadiazolopyridine Ethyl Ester (13)

In a 500 ml three-neck flask, 10.0 g (0.033 mol) of the oxadiazole dibenzoyl (12) was dissolved in 300 ml of butanol. To this, 32.0 g (0.23 mol) of glycine ethyl ester hydrochloride was added. The obtained mixture was refluxed under heating for 24 hours. Butanol was distilled off under reduced pressure to obtain a residue. The residue was dissolved in 200 ml of chloroform and washed with 10% hydrochloric acid, then with saturated sodium bicarbonate, and with an aqueous 10%

Scheme 10

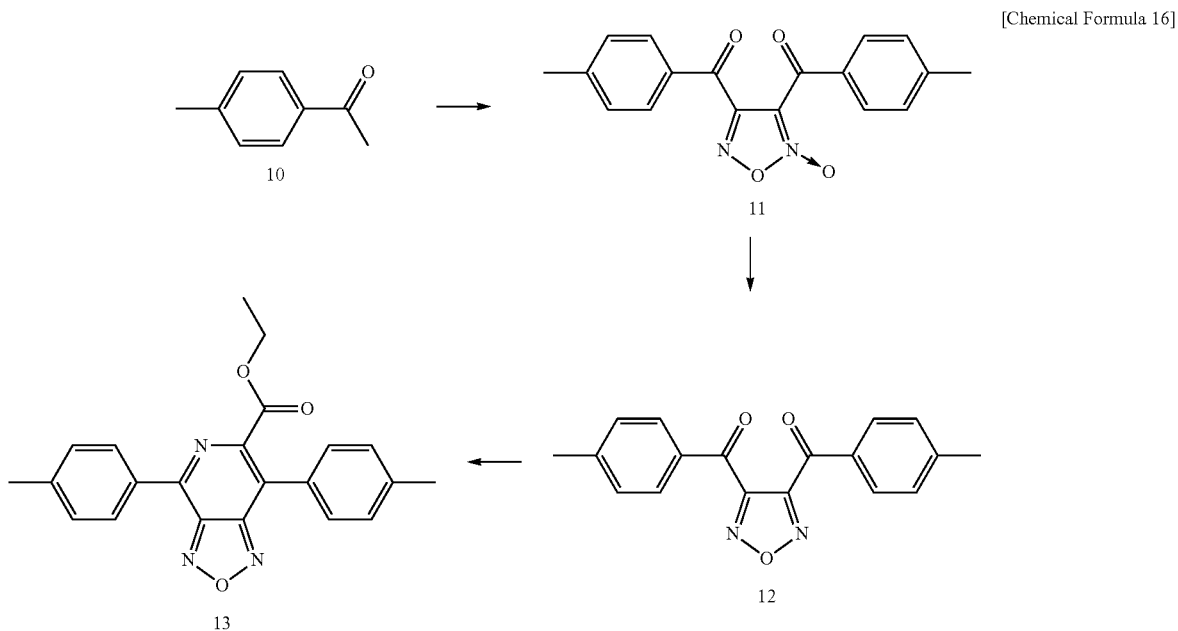

[Chemical Formula 16]

(1) Synthesis of a Diketone Derivative (11)

In a 500 ml three-neck flask, 30.0 g (0.22 mol) of 4-methoxyacetophenone (10) and 0.15 g of sodium nitrite were dissolved in 100 ml of acetic acid. A solution prepared by dissolving 100 ml of nitric acid in 100 ml of acetic acid was added dropwise to the solution in a water bath over 1 hour. Then, the obtained solution was stirred at room temperature for 2 days. The reaction mixture was gradually poured into 500 ml of water to produce a precipitate. The precipitate was filtrated and dissolved in chloroform. The chloroform phase was washed with saturated sodium bicarbonate water, and also washed twice with an aqueous 10% NaCl solution. The washed precipitate was dehydrated over magnesium sulfate anhydride, and then chloroform was distilled off under reduced pressure to obtain oxadiazole-N-oxide (11) (yield amount: 26.6 g, yield: 75%).

NaCl solution. The washed residue was dried over magnesium sulfate anhydride to remove the solvent. The obtained residue was recrystallized from chloroform to obtain a 4,7-di(methylphenyl)-1,2,5-oxadiazolopyridine ethyl ester (13) (hereinafter referred to as an ester (13)) (yield amount: 8.6 g, yield: 70%).

Then, the ester (13) was subjected to a reducing reaction in the presence of NaBH$_4$ to obtain a diamino alcohol (14). The obtained alcohol (14) was reacted with thionyl chloride to obtain a thiadiazolopyridine chloromethyl (15). The obtained thiadiazolopyridine chloromethyl (15) was reacted with triphenylphosphine to obtain a phosphonium salt (16), which was then subjected to a Wittig reaction to obtain a vinyl so that a pyridinium salt containing an active ester was synthesized.

Scheme 11

[Chemical Formula 17]

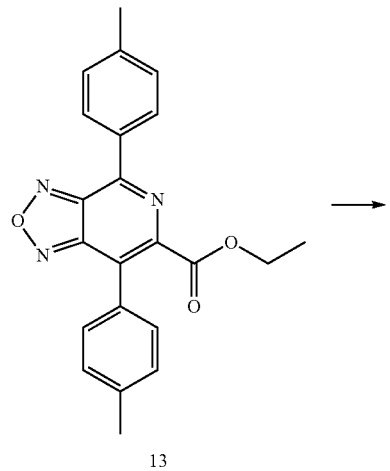

13

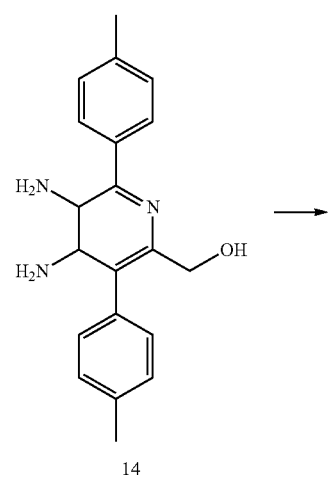

14

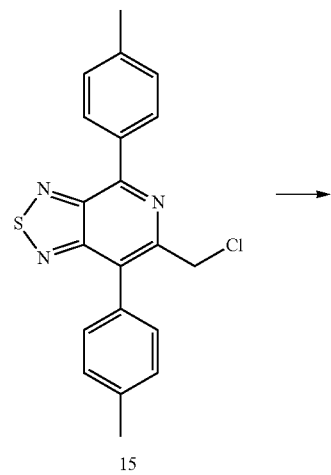

15

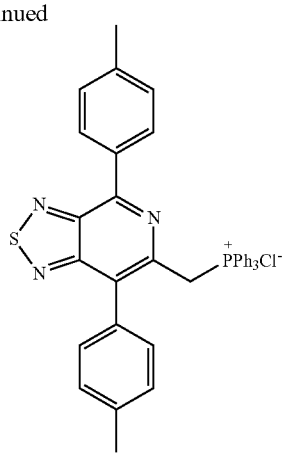

16

(4) Synthesis of a Diamino Alcohol (14)

A solution (100 ml) of the ester (13) (1.86 g, 5 mmol) and NaBH$_4$ (1.30 g, 35 mmol) in ethanol was refluxed under heating for 8 hours. Then, the reaction solution was poured into water, which was allowed to stand overnight. Then, the precipitate was filtrated to obtain a diamino alcohol (14) (yield amount: 1.41 g, yield: 88%).

(5) Synthesis of a Chloromethyl (15)

Thionyl chloride (5 ml) and pyridine-NaBH$_4$ (3 ml) were added dropwise in this order to a solution (50 ml) of 1.20 g (3.7 mmol) of the alcohol (14) in chloroform, and the mixture was refluxed under heating for 3 hours. Then, the reaction solution was poured into water, which was neutralized with saturated sodium bicarbonate and extracted with chloroform. The extract was dried over magnesium sulfate anhydride and the residue obtained after distillation under reduced pressure was subjected to column treatment to obtain a chloromethyl (15) (yield amount: 1.08 g, yield: 80%).

(6) Synthesis of a Phosphonium Salt (16)

A solution (6 ml) of the chloromethyl (15) (146 mg, 0.40 mmol) and triphenylphosphine (115 mg, 0.044 mmol) in toluene was refluxed under heating for 2 days and the precipitate was filtrated and washed with ether to obtain a phosphonium salt (16) (yield amount: 116 mg, yield: 46%).

The phosphonium salt (16) was used to synthesize a 4-vinylpyridinium salt containing an active ester. An example of reaction will be shown below.

Scheme 12

[Chemica Formula 18]

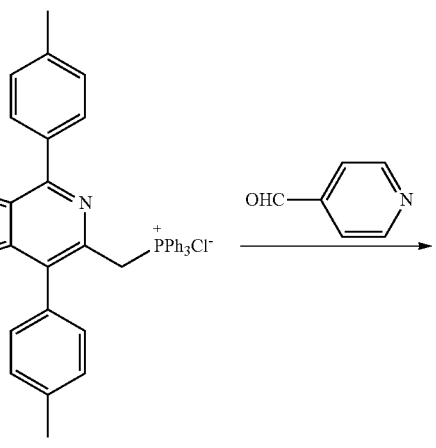

Scheme 13

[Chemical Formula 19]

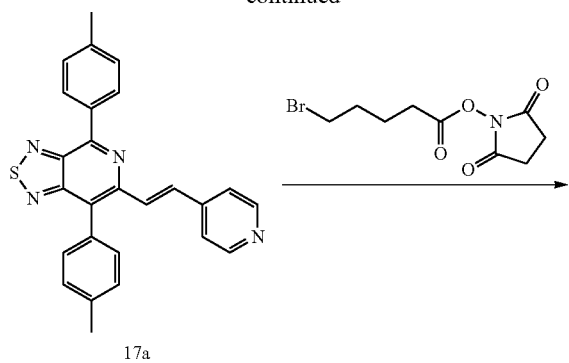

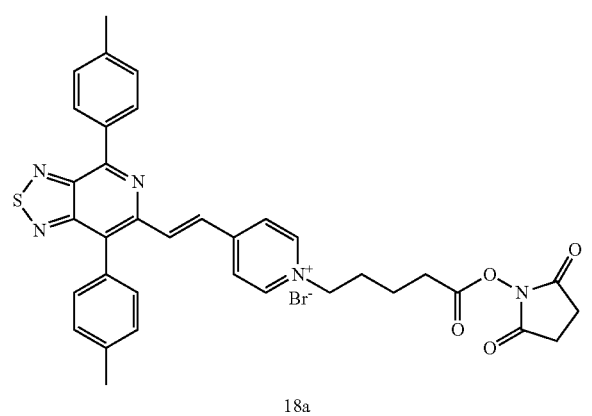

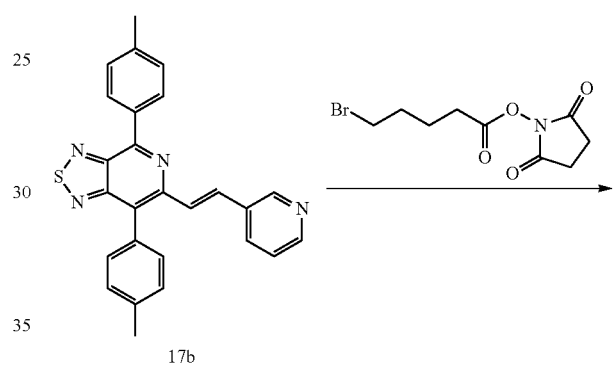

(7) Synthesis of a Vinyl (17a)

p-Formylpyridine (24 µL, 0.26 mmol) was added to a solution (3 ml) of the phosphonium salt (16) (150 mg, 0.24 mmol) and potassium hydroxide (purity: 85%, 30 mg) in ethanol under ice-cooling, and the mixture was stirred at the temperature for 1 hour and then at room temperature for 1 hour. The precipitate was filtrated and subjected to column treatment to obtain 4,7-di(methylphenyl)-1,2,5-thiadiazolopyridine-6-(4-vinylpyridine) (hereinafter referred to as a vinyl (17a)) (yield amount: 53 mg, yield: 53%).

(8) Synthesis of a Pyridinium Salt (18a) Containing an Active Ester

A solution (3 ml) of the vinyl (17a) (50 mg, 0.12 mmol) and a bromohexanoic acid active ester (36 mg, 0.08 mol) in toluene was refluxed under heating for 3 days, and then the precipitate was filtrated to obtain a 4-vinylpyridinium salt (18a) containing an active ester.

Synthetic Example 7

A 3-vinylpyridinium salt containing an active ester was synthesized by using, as a starting material, the phosphonium salt (16) synthesized in Synthetic Example 6. An example of synthesis will be shown below.

(1) Synthesis of a Vinyl (17b)

m-Formylpyridine (26 µL, 0.28 mmol) was added to a solution (4 ml) of the phosphonium salt (16) (150 mg, 0.25 mmol) and potassium hydroxide (purity: 85%, 30 mg) in ethanol under ice-cooling, and the mixture was stirred at the temperature for 1 hour and then at room temperature for 2 hours. The precipitate was filtrated and subjected to column treatment to obtain 4,7-di(methylphenyl)-1,2,5-thiadiazolopyridine-6-(3-vinylpyridine) (hereinafter referred to as a vinyl (17b)) (yield amount: 54 mg, yield: 51%).

(2) Synthesis of a Pyridinium Salt (18b) Containing an Active Ester

A solution (5 ml) of the vinyl (17b) (50 mg, 0.12 mmol) and a bromohexanoic acid active ester (37 mg, 0.11 mol) in toluene was refluxed under heating for 5 days, and then the precipitate was filtrated to obtain a 3-vinylpyridinium salt (18b) containing an active ester.

Synthetic Example 8

A 2-vinylpyridinium salt containing an active ester was synthesized by using, as a starting material, the phosphonium salt (16) synthesized in Synthetic Example 6. An example of synthesis will be shown below.

Scheme 14

[Chemica Formula 20]

(1) Synthesis of a Vinyl (17c)

o-Formylpyridine (16 μL, 0.18 mmol) was added to a solution (4 ml) of the phosphonium salt (16) (100 mg, 0.16 mmol) and potassium hydroxide (purity: 85%, 30 mg) in ethanol under ice-cooling, and the mixture was stirred at the temperature for 1 hour and then at room temperature for 1 hour. The precipitate was filtrated and subjected to column treatment to obtain 4,7-di(methylphenyl)-1,2,5-thiadiazolopyridine-6-(2-vinylpyridine) (hereinafter referred to as a vinyl (17c)) (yield amount: 54 mg, yield: 80%).

(2) Synthesis of a Pyridinium Salt (18c) Containing an Active Ester

A solution (3 ml) of the vinyl (17c) (50 mg, 0.12 mmol) and a bromohexanoic acid active ester (36 mg, 0.13 mol) in toluene was refluxed under heating for 3 days, and then the precipitate was filtrated to obtain a 2-vinylpyridinium salt (18c) containing an active ester.

Synthetic Example 9

An example of synthesis of an active ester of 4,7-di(methylthienyl)-1,2,5-oxadiazolopyridine-6-(3-pyridinium) will be shown below.

Scheme 15

[Chemical Formula 21]

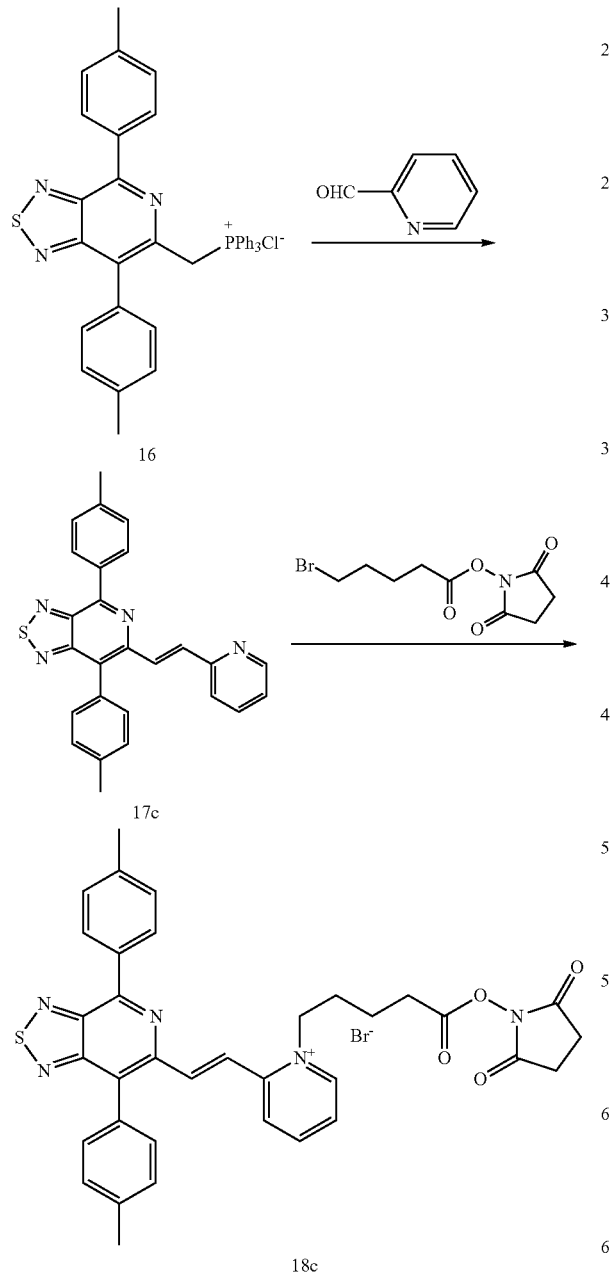

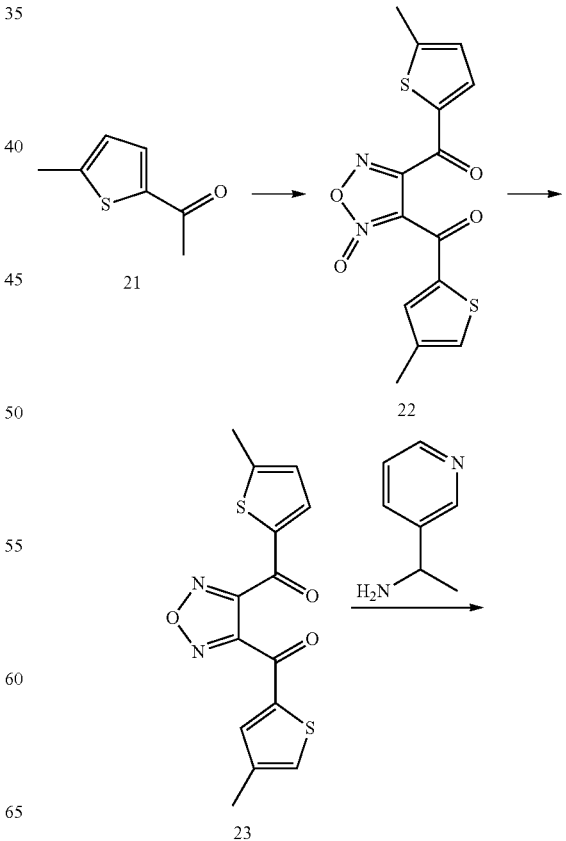

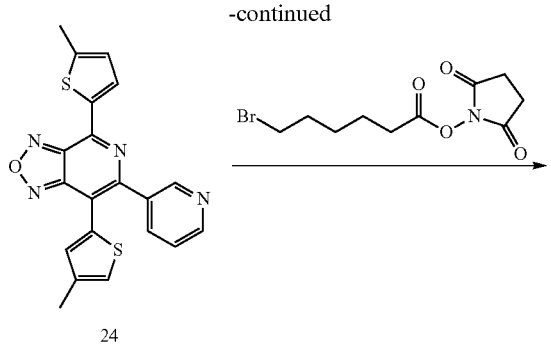

(1) Synthesis of a Diketone (22)

in a three-neck flask, 25.00 g (0.18 mol) of 2-acetyl-5-methylthiophene (21) and 0.40 g of sodium nitrite were put and dissolved in 40 ml of acetic acid with stirring. Next, a mixture solution of 30 ml of nitric acid and 40 ml of acetic acid was added dropwise to the reaction solution over 2 hours. After the dropwise addition, the reaction solution was allowed to stand with stirring for 2 days. The reaction product was subjected to suction filtration, and the supernatant was washed with water and dried by a dryer for 2 days. The dried product was recrystallized from ethanol to obtain a diketone (22) (yield amount: 20.3 g, yield: 68%).

(2) Synthesis of a Diketone (23)

In 190 ml of acetonitrile, 5.00 g (0.015 mol) of the diketone (22) was dissolved. After the dissolution, 1.50 ml of acetic acid and 4.38 ml of acetic acid anhydride were added to the solution, and the obtained mixture was then stirred at 40° C. Next, 6.84 g of a zinc powder was poured into the mixture to undergo reaction for 30 minutes, and then zinc was filtrated on celite by suction filtration. The solvent was distilled off under reduced pressure, and the residue was dissolved in chloroform. The residue was then washed with saturated sodium bicarbonate water and aqueous hydrochloric acid in this order, and dried over magnesium sulfate, followed by distillation under reduced pressure. The residue was separated/purified by column chromatography, and then recrystallized from ethanol to obtain a diketone (23) (yield amount: 2.76 g, yield: 58%).

(3) Synthesis of a Pyridyl (24)

In an eggplant flask, 1.00 g (0.003 mol) of the diketone (23) and 90 ml of ethanol were added and heated to 60° C. to dissolve. In this, 2.56 g (0.02 mmol) of 3-picolylamine was dissolved. Next, 7.00 ml of triethylamine was poured into the solution, which was then refluxed under heating for 18 hours. After ethanol was distilled off under reduced pressure, the residue was washed with aqueous hydrochloric acid and saturated sodium bicarbonate water in this order, and then dried under reduced pressure. The residue was then separated by column chromatography. The obtained residue was recrystallized from ethanol to obtain 4,7-di(methylthienyl)-1,2,5-oxadiazolopyridine-6-(3-pyridine) (hereinafter referred to as a pyridyl (24)) (yield amount: 0.75 g, yield: 64%).

(4) Synthesis of an Active Ester (25)

In 6 ml of toluene, 200 mg (0.51 mmol) of the pyridyl (24) and 148 mg (0.51 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (25).

Synthetic Example 10

An active ester was synthesized by using a bromopropionic acid active ester in place of the bromohexanoic acid active ester in Synthetic Example 9. An example of synthesis will be shown below.

Scheme 16

[Chemical Formula 22]

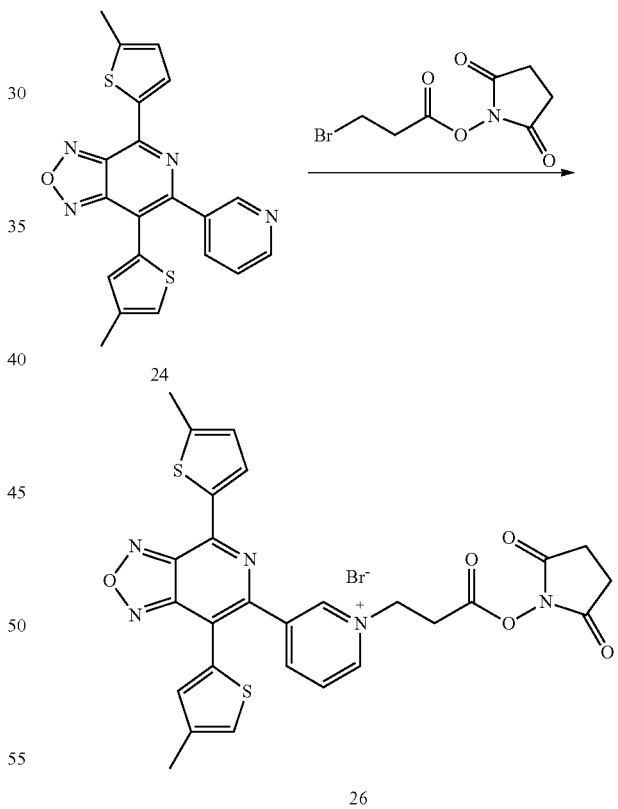

(1) Synthesis of an Active Ester (26)

In 6 ml of toluene, 200 mg (0.51 mmol) of the pyridyl (24) and 127 mg (0.51 mmol) of a bromopropionic acid active ester were dissolved, and the obtained mixture was then stirred at room temperature overnight. After the reaction was completed, the reaction mixture was subjected to suction filtration and the filtrated product was dried under vacuum to obtain an active ester (26).

Synthetic Example 11

An example of synthesis of an active ester of 4,7-di(methylthienyl)-1,2,5-oxadiazolopyridine-6-(4-pyridinium) will be shown below.

Scheme 17

[Chemical Formula 23]

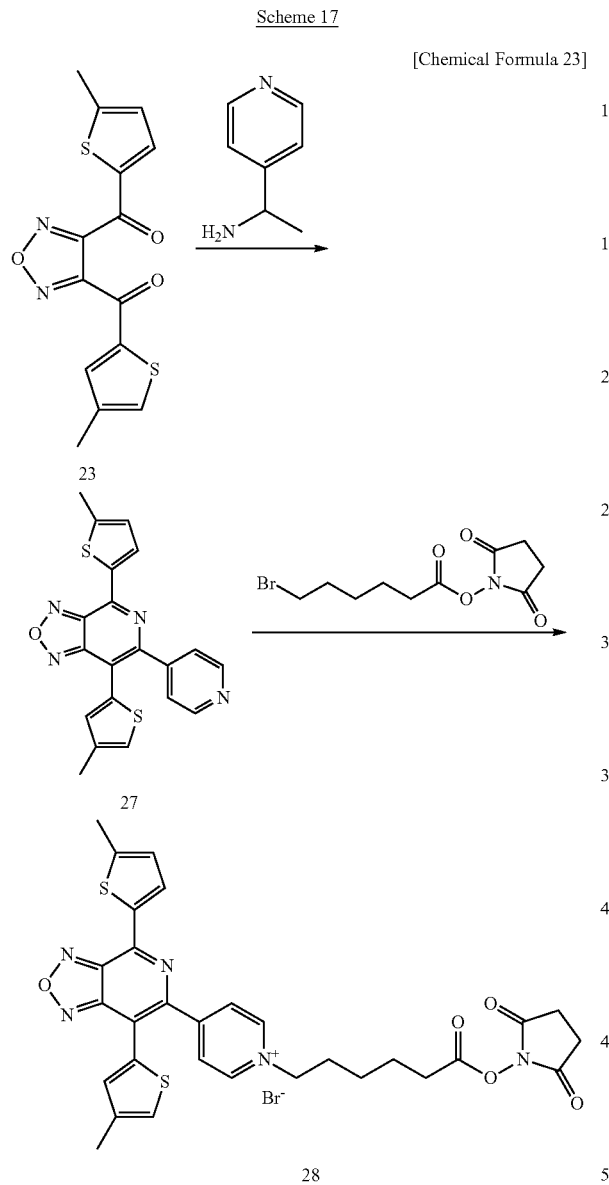

(1) Synthesis of a Pyridyl (27)

In an eggplant flask, 1.00 g (0.003 mol) of the diketone (23) and 90 ml of ethanol were added and heated to 60° C. to dissolve. In this, 2.56 g (0.02 mmol) of 4-picolylamine was dissolved. Next, 7.00 ml of triethylamine was poured into the solution, which was then refluxed under heating for 15 hours. After ethanol was distilled off under reduced pressure, the residue was washed with aqueous hydrochloric acid and saturated sodium bicarbonate water in this order, and then dried under reduced pressure. The residue was then separated by column chromatography. The obtained residue was recrystallized from ethanol to obtain 4,7-di(methylthienyl)-1,2,5-oxadiazolopyridine-6-(4-pyridine) (hereinafter referred to as a pyridyl (27)) (yield amount: 0.67 g, yield: 57%).

(2) Synthesis of an Active Ester (28)

In 9 ml of toluene, 300 mg (0.77 mmol) of the pyridyl (27) and 214 mg (0.77 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (28).

Synthetic Example 12

An active ester was synthesized by using a phenyl group in place of the thienyl group. An example of synthesis will be shown below.

Scheme 18

[Chemical Formula 24]

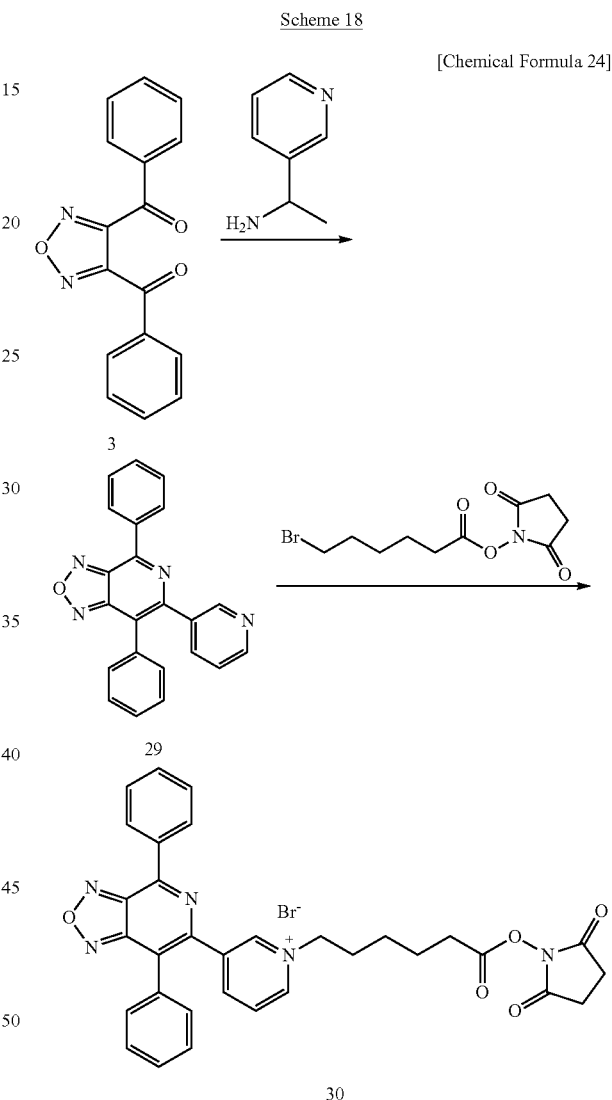

(1) Synthesis of a Pyridyl (29)

In 25 ml of dioxane, 300 mg (1.08 mmol) of the diketone (3) and 1 ml (10 mmol) of 3-picolylamine were dissolved, and then the obtained mixture was refluxed under heating for 2 days. After the reaction was completed, the reaction mixture was distilled off under reduced pressure, and then purified by silica gel column chromatography to fractionate an object product. The obtained product was further recrystallized from ethanol to obtain 4,7-diphenyl-1,2,5-oxadiazolopyridine-6-(3-pyridine) (hereinafter referred to as a pyridyl (29)) (yield amount: 324.80 mg, yield: 48%).

(2) Synthesis of an Active Ester (30)

In 6 ml of toluene, 200 mg (0.57 mmol) of the pyridyl (29) and 158 mg (0.57 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (30).

Synthetic Example 13

An example of synthesis of an active ester of 4,7-di(bromothienyl)-1,2,5-oxadiazolopyridine-6-(4-pyridine) will be shown below.

Scheme 19

[Chemical Formula 25]

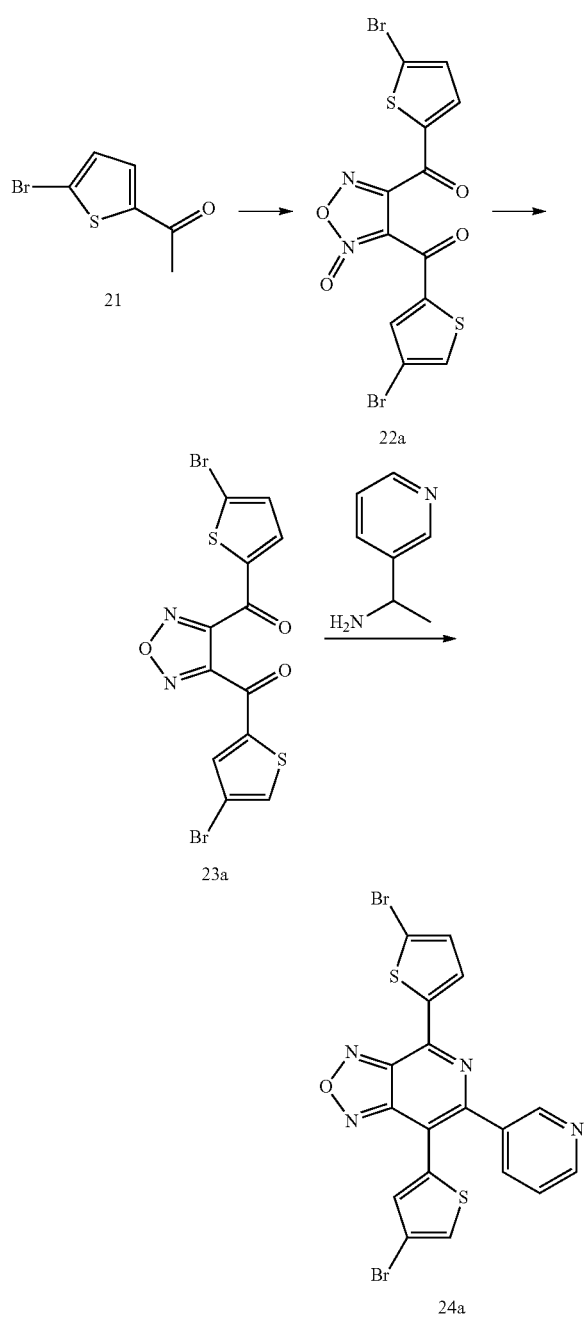

(1) Synthesis of a Diketone (22a)

In a three-neck flask, 20.00 g (0.10 mol) of 2-acetyl-5-bromothiophene (21) and 0.30 g of sodium nitrite were put and dissolved in 40 ml of acetic acid with stirring. Next, a mixture solution of 30 ml of nitric acid and 40 ml of acetic acid was added dropwise to the reaction solution over 2 hours. After the dropwise addition, the reaction solution was allowed to stand with stirring for 2 days. The reaction product was subjected to suction filtration, and the supernatant was washed with water and dried by a dryer for 2 days. The dried product was recrystallized from ethanol to obtain a diketone (22a) (yield amount: 26.3 g, yield: 58%).

(2) Synthesis of a Diketone (23a)

In 150 ml of acetonitrile, 5.00 g (0.011 mol) of the diketone (22a) was dissolved. After the dissolution, 1.50 ml of acetic acid and 4.0 ml of acetic acid anhydride were added to the solution, and the obtained mixture was then stirred at 40° C. Then, 6.0 g of a zinc powder was poured into the mixture to undergo a reaction for 30 minutes, and then zinc was filtrated on celite by suction filtration. The solvent was distilled off under reduced pressure, and the residue was dissolved in chloroform. The residue was then washed with saturated sodium bicarbonate water and aqueous hydrochloric acid in this order, and dried over magnesium sulfate, followed by distillation under reduced pressure. The residue was separated/purified by column chromatography, and then recrystallized from ethanol to obtain a diketone (23a) (yield amount: 2.67 g, yield: 55%).

(3) Synthesis of a Pyridyl (24a)

In an eggplant flask, 2.00 g (0.004 mol) of the diketone (23a) was added with 90 ml of ethanol, and the mixture was heated to 60° C. to dissolve. In this, 2.56 g (0.02 mmol) of 4-picolylamine was dissolved. Next, 7.00 ml of triethylamine was poured into the solution, which was then refluxed under heating for 24 hours. After ethanol was distilled off under reduced pressure, the residue was washed with aqueous hydrochloric acid and saturated sodium bicarbonate water in this order, and then dried under reduced pressure. The residue was then separated by column chromatography. The obtained residue was recrystallized from ethanol to obtain 4,7-di(bromothienyl)-1,2,5-oxadiazolopyridine-6-(4-pyridine) (hereinafter referred to as a pyridyl (24a)) (yield amount: 1.18 g, yield: 51%).

(4) Synthesis of an Active Ester

In 6 ml of toluene, 200 mg (0.57 mmol) of the pyridyl (24a) and 158 mg (0.57 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester.

Synthetic Example 14

An example of synthesis of an active ester of 4,7-di[(2-phenyl)thienyl]-1,2,5-oxadiazolopyridine-6-(4-pyridinium) will be shown below.

Scheme 20

[Chemical Formula 26]

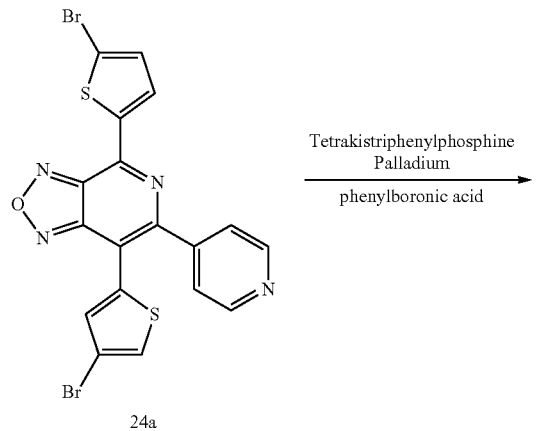

24a

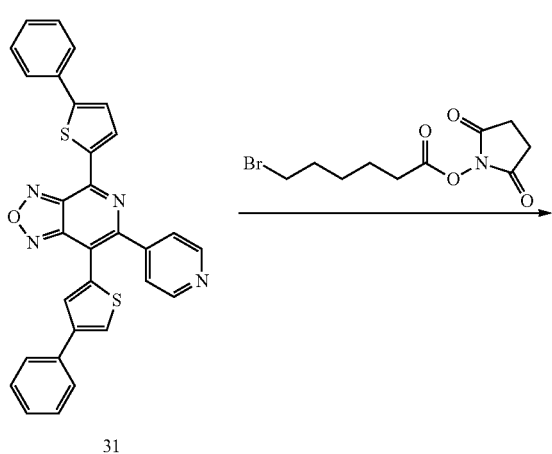

31

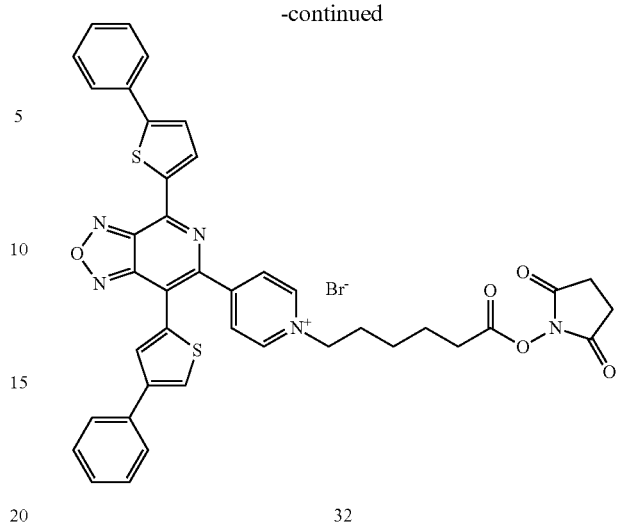

32

(1) Synthesis of a Pyridyl (31) Using Suzuki Coupling

In an eggplant flask in which the atmosphere was replaced with argon, 200 mg (0.38 mmol) of the pyridyl (24a) and 12.7 mg of tetrakis triphenylphosphine palladium were placed and dissolved in 2.8 ml of an aqueous 2M-sodium carbonate solution and 4 ml of benzene. In 2 ml of ethanol, 99 mg (0.83 mmol) of phenylboronic acid was dissolved, and the obtained mixture was poured into the reaction solution. Thereafter, the reaction solution was refluxed under heating at 80° C. for 5 hours. Into the reaction solution, 20 ml of water was poured for extraction using chloroform. Chloroform was distilled off under reduced pressure and the residue was recrystallized from hexane-chloroform. A pyridyl (31) was thus obtained in a yield amount of 120 mg and in a yield of 61%.

(2) Synthesis of an Active Ester (32)

In 8 ml of toluene, 300 mg (0.58 mmol) of the pyridyl (31) and 170 mg (0.58 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (32).

Synthetic Example 15

An example of synthesis of an active ester of 4,7-di[(1-naphthyl)thienyl]-1,2,5-oxadiazolopyridine-6-(4-pyridinium) will be shown below.

Scheme 21
[Chemical Formula 27]
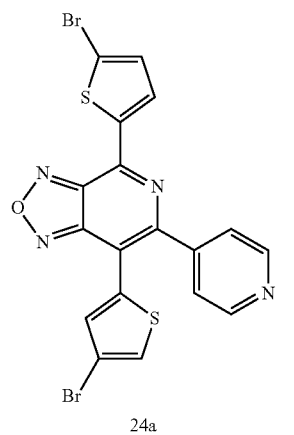
24a
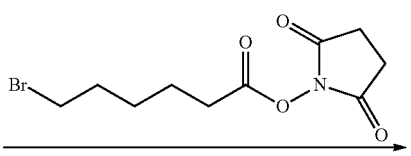
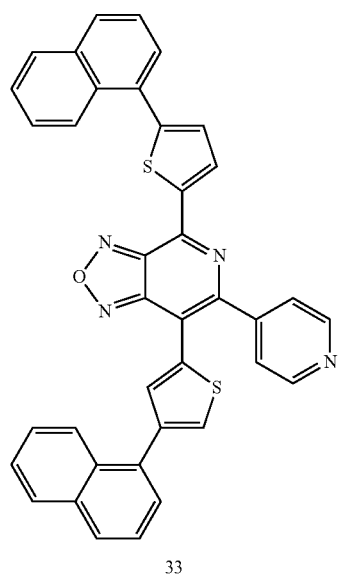
33
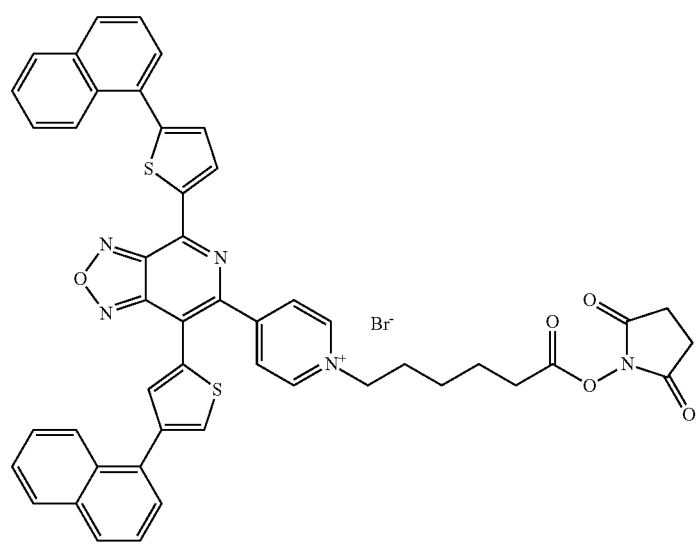
34

(1) Synthesis of a Pyridyl (33) Using Suzuki Coupling

In an eggplant flask in which the atmosphere was replaced with argon, 200 mg (0.38 mmol) of the pyridyl (24a) and 12.7 mg of tetrakis triphenylphosphine palladium were placed and dissolved in 2.8 ml of an aqueous 2M-sodium carbonate solution and 4 ml of benzene. In 2 ml of ethanol, 144 mg (0.83 mmol) of 1-naphthylboronic acid was dissolved, and the obtained mixture was poured into the reaction solution. Thereafter, the reaction solution was refluxed under heating at 80° C. for 6 hours. Into the reaction solution, 20 ml of water was poured for extraction using chloroform. Chloroform was distilled off under reduced pressure and the residue was recrystallized from hexane-chloroform. A pyridyl (33) was thus obtained in a yield amount of 190 mg and in a yield of 55%.

(2) Synthesis of an Active Ester (34)

In 8 ml of toluene, 300 mg (0.58 mmol) of the pyridyl (33) and 170 mg (0.58 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (34).

Synthetic Example 16

An example of synthesis of an active ester of 4,7-di[(2-naphthyl)thienyl]-1,2,5-oxadiazolopyridine-6-(4-pyridinium) will be shown below.

Scheme 22

[Chemical Formula 28]

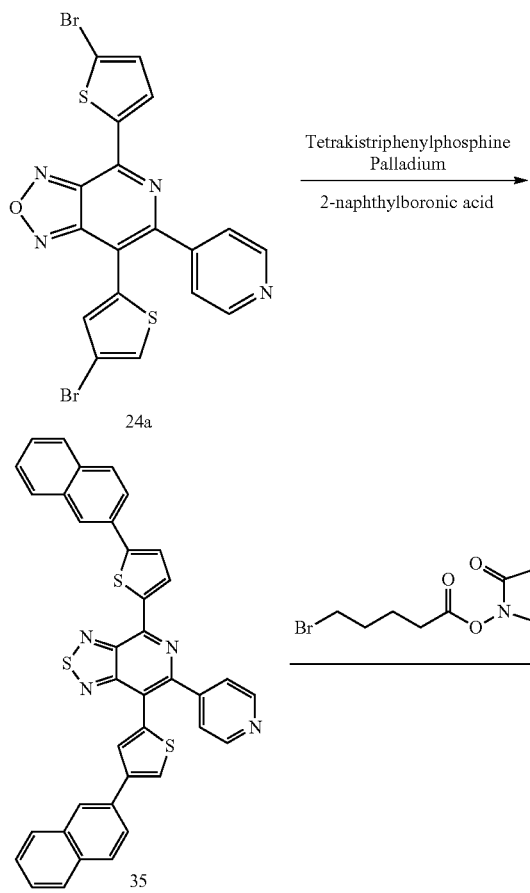

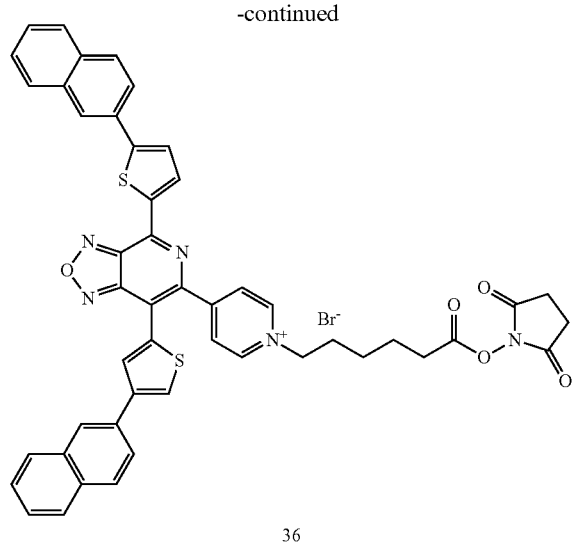
36

(1) Synthesis of a Pyridyl (35) Using Suzuki Coupling in an eggplant flask in which the atmosphere was replaced with argon, 200 mg (0.38 mmol) of the pyridyl (24a) and 12.7 mg of tetrakis triphenylphosphine palladium were placed and dissolved in 2.8 ml of an aqueous 2M-sodium carbonate solution and 4 ml of benzene. In 2 ml of ethanol, 144 mg (0.83 mmol) of 2-naphthylboronic acid was dissolved, and the obtained mixture was poured into the reaction solution. Thereafter, the reaction solution was refluxed under heating at 80° C. for 5 hours. Into the reaction solution, 15 ml of water was poured for extraction using chloroform. Chloroform was distilled off under reduced pressure and the residue was recrystallized from hexane-chloroform. A pyridyl (35) was thus obtained in a yield amount of 220 mg and in a yield of 64%.

(2) Synthesis of an Active Ester (36)

In 8 ml of toluene, 300 mg (0.58 mmol) of the pyridyl (35) and 170 mg (0.58 mmol) of a bromohexanoic acid active ester were dissolved, and the obtained mixture was then stirred at room temperature overnight. After the reaction was completed, the reaction mixture was subjected to suction filtration and the filtrated product was dried under vacuum to obtain an active ester (36).

Synthetic Example 17

An example of synthesis of an active ester of 4,7-di[(2-bromo)thienyl]-1,2,5-oxadiazolopyridine-6-(4-vinylpyridinium) will be shown below.

Scheme 23

[Chemical Formula 29]

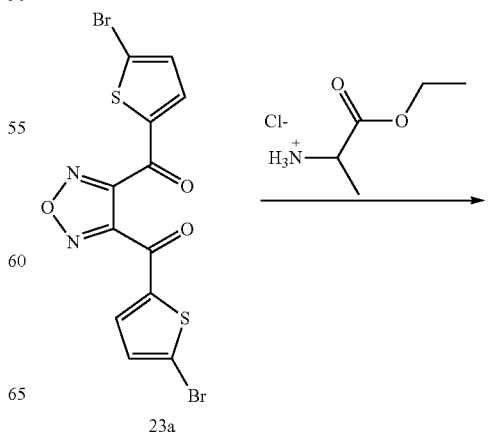

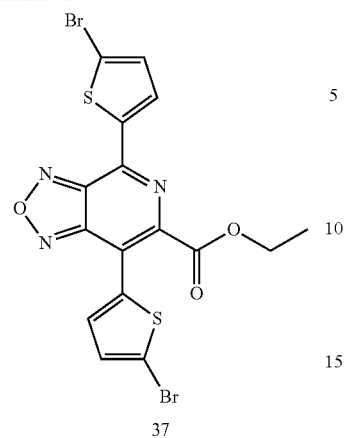

37

(1) Synthesis of an Ethyl Ester (37)

To a 200 ml three-neck flask, 2.0 g (4.5 mmol) of the diketone (23a) and 90 ml of ethanol were added and heated to 60° C. to dissolve. In this, 4.8 g (31.4 mmol) of glycine ethyl ester hydrochloride was dissolved. Next, 7 ml of triethylamine was poured into the solution, which was then refluxed under heating for 24 hours. Ethanol was distilled off under reduced pressure, and then the residue was washed with aqueous hydrochloric acid and saturated sodium bicarbonate water in this order, followed by drying under reduced pressure. The residue was separated by column chromatography. The residue was recrystallized from ethanol to obtain 4,7-di (bromothienyl)-1,2,5-oxadiazolopyridine-6-ethyl ester (hereinafter referred to as an ethyl ester (37)) in a yield amount of 1.18 g and in a yield of 51%.

Scheme 24

[Chemical Formula 30]

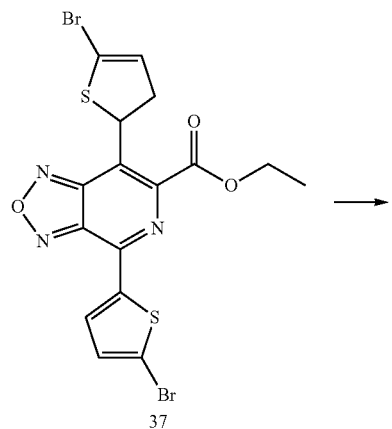

37

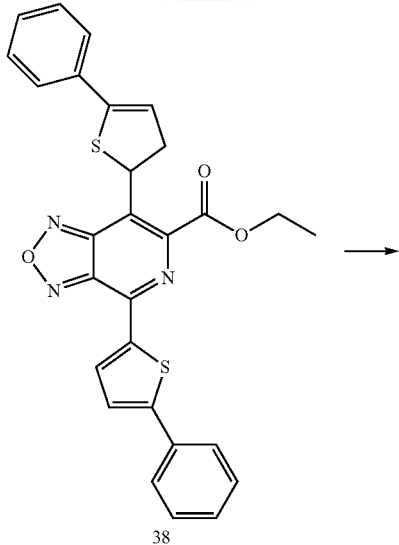

38

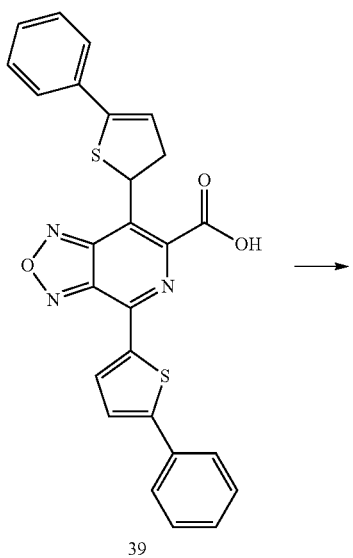

39

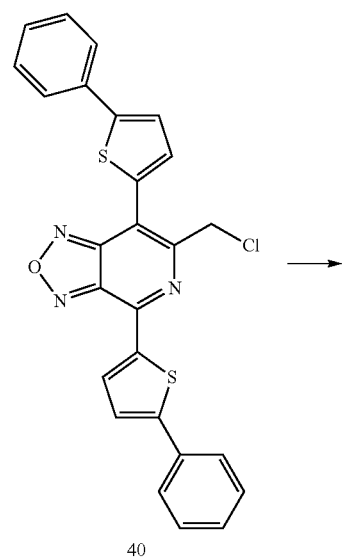

40

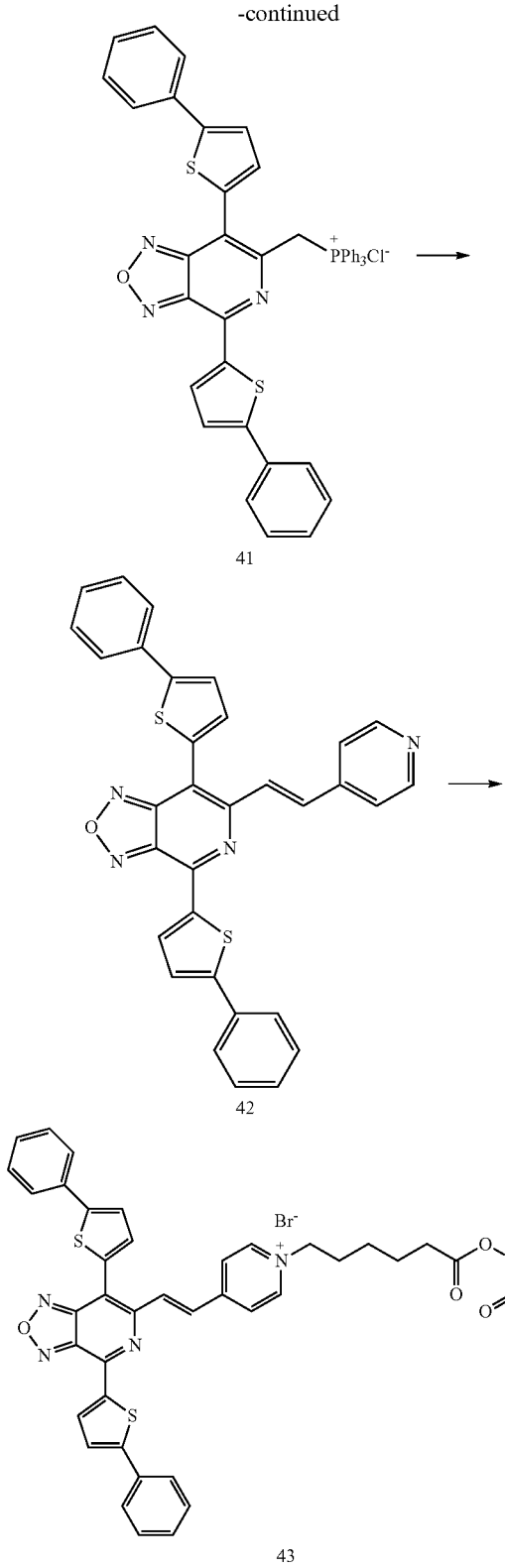

(1) Synthesis of an Ethyl Ester (38) Using Suzuki Coupling

In an eggplant flask in which the atmosphere was replaced with argon, 195 mg (0.38 mmol) of the ethyl ester (30) and 12.7 mg of tetrakis triphenylphosphine palladium were placed and dissolved in 2.8 ml of an aqueous 2M-sodium carbonate solution and 4 ml of benzene. In 2 ml of ethanol, 101 mg (0.83 mmol) of phenylboronic acid was dissolved, and the obtained mixture was poured into the reaction solution. Thereafter, the reaction solution was refluxed under heating at 80° C. for 5 hours. Into the reaction solution, 15 ml of water was poured for extraction using chloroform. Chloroform was distilled off under reduced pressure and the residue was recrystallized from hexane-chloroform. An ethyl ester (38) was thus obtained in a yield amount of 112 mg and in a yield of 58%.

(2) Synthesis of a Hydroxymethyl (39)

A solution of DOBAL (manufactured by Sigma Aldrich, concentration 1.5 M, 6 µL) in toluene was added dropwise to a solution (3 ml) of the ester (38) (255 mg, 0.50 mmol) in THF under ice-cooling, and the mixture was stirred under ice-cooling for 30 minutes, and subsequently at room temperature for 30 minutes. Then, the reaction solution was poured into water, which was put into an acidic state (precipitate disappeared) by adding an aqueous 3% HCl to be extracted with chloroform. The extract was dried over $MgSO_4$, and the residue obtained after distillation under reduced pressure was dispersed in silica gel (Kanto C-60), which was then heated at 80° C. overnight. This silica gel was washed with ethyl acetate (AcOEt), and the residue obtained by distilling the washed solution under reduced pressure was subjected to column treatment (Kanto C-60, Hexane/AcOEt=2/1 (v/v)) to obtain a hydroxymethyl (39) in a yield amount of 89 mg and in a yield of 38%.

(3) Synthesis of a Chloromethyl (40)

A solution (3 ml) of the hydroxymethyl (39) (100 mg) and $SOCl_2$ (3 ml) in chloroform was refluxed under heating for 2 hours. The reaction solution was poured into water, which was neutralized with $NaHCO_3$ and then extracted with chloroform. The extract was dried over $MgSO_4$ and the residue obtained after distillation under reduced pressure was subjected to column treatment (Kanto C-60; Hexane/$CHCl_3$=5/1 (v/v)) to obtain a chloromethyl (40) in a yield amount of 102 mg.

(3) Synthesis of a Phosphonium Salt (41)

A solution (3 ml) of the chloromethyl (40) (107 mg, 0.22 mmol) and Ph3P (63 mg, 0.24 mmol) in toluene was refluxed under heating for 24 hours. The precipitate was filtrated to obtain a phosphonium salt (41) in a yield amount of 97 mg and in a yield of 59%.

(4) Synthesis of a Vinyl (42)

p-Formylpyridine (29 µL, 0.31 mmol) was added to a solution (3 ml) of the phosphonium salt (41) (210 mg, 0.28 mmol) and potassium hydroxide (purity: 85%, 30 mg) in ethanol under ice-cooling, and the mixture was stirred at the temperature for 1 hour and subsequently at room temperature for 1 hour. The precipitate was filtrated and subjected to column treatment (Kanto C-60; $CHCl_3$/AcOEt=10/1 (v/v)) to obtain a vinyl (42) in a yield amount of 118 mg and in a yield of 78%.

(5) Synthesis of an Active Ester (43)

A solution (2 ml) of the vinyl (42) (108 mg, 0.20 mmol) and a bromohexanoic acid active ester (63 mg, 0.22 mmol) in toluene was refluxed under heating for 2 days. The precipitate was filtrated to obtain an active ester (43) of a pyridinium salt.

Synthetic Example 18

An example of synthesis of an active ester of 4,7-di[(1-naphthyl)thienyl]-1,2,5-oxadiazolopyridine-6-(4-vinylpyridinium) will be shown below.

Scheme 25
[Chemical Formula 31]
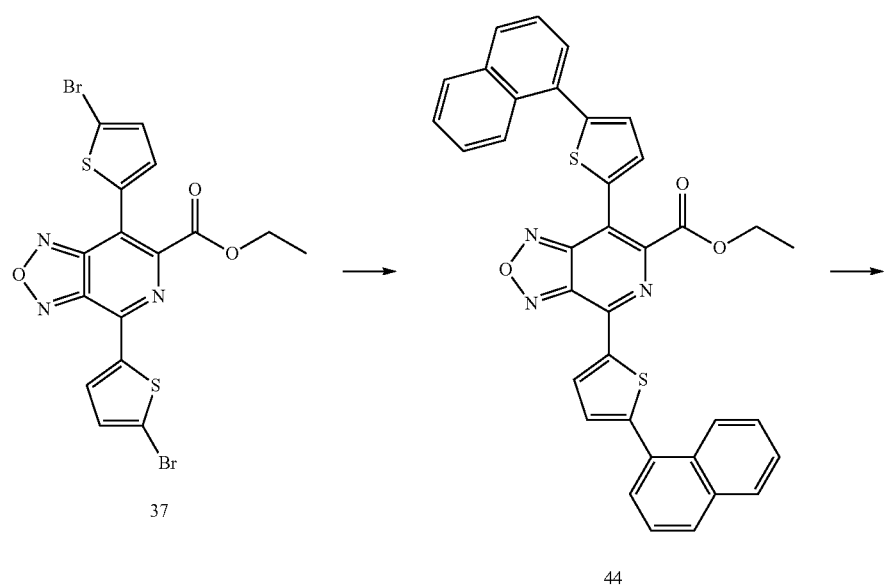
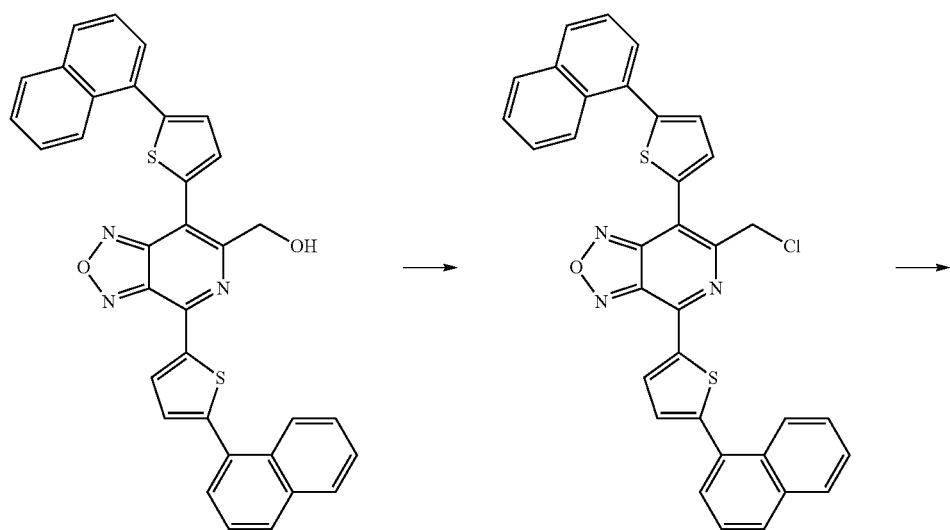

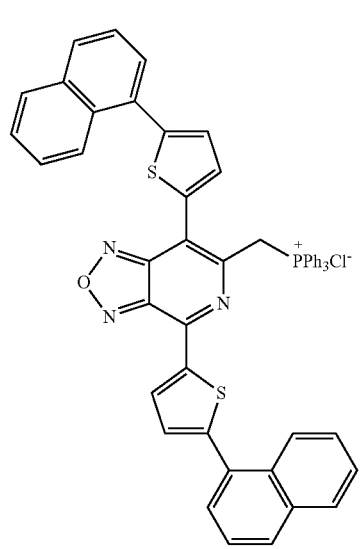

47

-continued

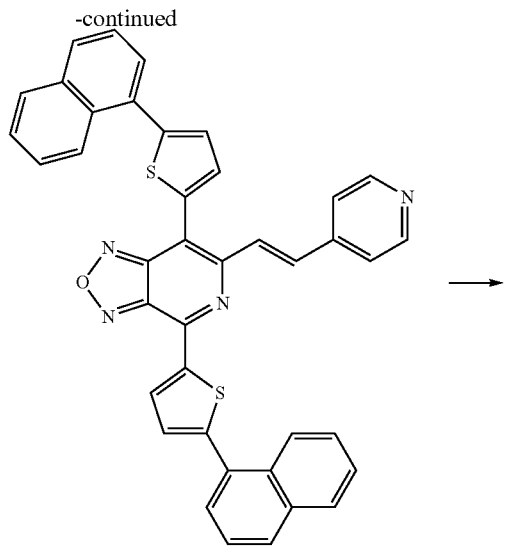

48

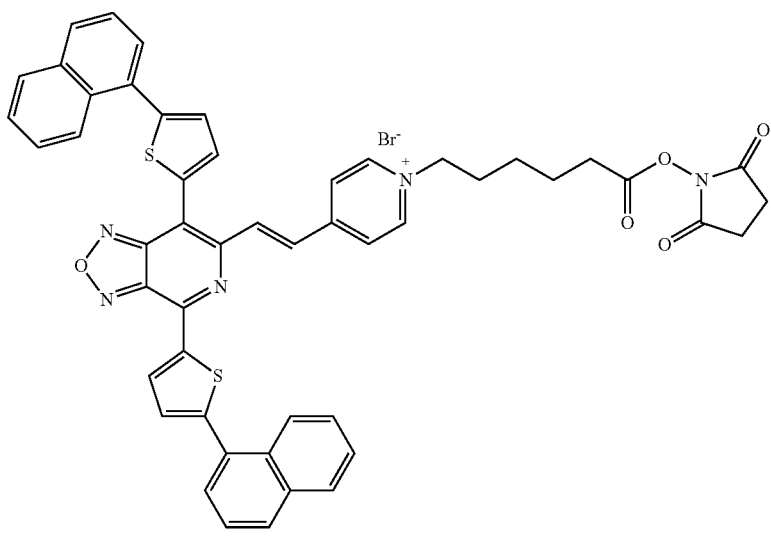

49

(1) Synthesis of an Ethyl Ester (44)

In an eggplant flask in which the atmosphere was replaced with argon, 216 mg (0.42 mmol) of the ethyl ester (37) and 14 mg of tetrakis triphenylphosphine palladium were placed and dissolved in 3 ml of 2M-sodium carbonate and 4.5 ml of benzene. In 2.5 ml of ethanol, 155 mg (0.90 mmol) of 1-naphthylboronic acid was dissolved, and the obtained mixture was poured into the reaction solution. Thereafter, the reaction solution was refluxed under heating at 80° C. for 7 hours. Into the reaction solution, 15 ml of water was poured for extraction using chloroform. Chloroform was distilled off under reduced pressure and the residue was recrystallized from hexane-chloroform. An ethyl ester (44) was thus obtained in a yield amount of 154 mg and in a yield of 60%.

(2) Synthesis of a Hydroxymethyl (45)

A solution of DIBAL (manufactured by Sigma Aldrich, concentration 1.5 M, 6 µL) in toluene was added dropwise to a solution (3 ml) of the ester (44) (268 mg, 0.44 mmol) in THF under ice-cooling, and the mixture was stirred under ice-cooling for 30 minutes, and subsequently at room temperature for 30 minutes. Then, the reaction solution was poured into water, which was put into an acidic state (precipitate disappeared) by adding an aqueous 3% HCl to be extracted with chloroform. The extract was dried over MgSO$_4$, and the residue obtained after distillation under reduced pressure was dispersed in silica gel (Kanto C-60), which was then heated at 80° C. overnight. This silica gel was washed with ethyl acetate (AcOEt), and the residue obtained by distilling the washed solution under reduced pressure was subjected to column treatment (Kanto C-60, Hexane/AcOEt=2/1 (v/v)) to obtain a hydroxymethyl (45) in a yield amount of 75 mg and in a yield of 30%.

(3) Synthesis of a Chloromethyl (46)

A solution (6 ml) of the hydroxymethyl (45) (200 mg) and SOCl$_2$ (6 ml) in chloroform was refluxed under heating for 2 hours. The reaction solution was poured into water, which was neutralized with NaHCO$_3$ and then extracted with chloroform. The extract was dried over MgSO$_4$ and the residue obtained after distillation under reduced pressure was subjected to column treatment (Kanto C-60; Hexane/CHCl$_3$=5/1 (v/v)) to obtain a chloromethyl (46) in a yield amount of 198 mg.

(4) Synthesis of a Phosphonium Salt (47)

A solution (3 ml) of the chloromethyl (46) (103 mg, 0.18 mmol) and Ph$_3$P (56 mg, 0.20 mmol) in toluene was refluxed under heating for 21 hours. The precipitate was filtrated to obtain a phosphonium salt (47) in a yield amount of 99 mg and in a yield of 65%.

(5) Synthesis of a Vinyl (48)

p-Formylpyridine (29 μL, 0.31 mmol) was added to a solution (3 ml) of the phosphonium salt (47) (238 mg, 0.28 mmol) and potassium hydroxide (purity: 85%, 30 mg) in ethanol under ice-cooling, and the mixture was stirred at the temperature for 1 hour and subsequently at room temperature for 1 hour. The precipitate was filtrated and subjected to column treatment (Kanto C-60; CHCl$_3$/AcOEt=10/1 (v/v)) to obtain a vinyl (48) in a yield amount of 126 mg and in a yield of 70%.

(6) Synthesis of an Active Ester (49)

A solution (2 ml) of the vinyl (48) (128 mg, 0.20 mmol) and a bromohexanoic acid active ester (63 mg, 0.22 mmol) in toluene was refluxed under heating for 2 days. The precipitate was filtrated to obtain an active ester (49) of a pyridinium salt.

Synthetic Example 19

An example of synthesis of an active ester of 4,7-di[(2-naphthyl)thienyl]-1,2,5-oxadiazolopyridine-6-(4-vinylpyridinium) will be shown below.

Scheme 26

[Chemical Formula 32]

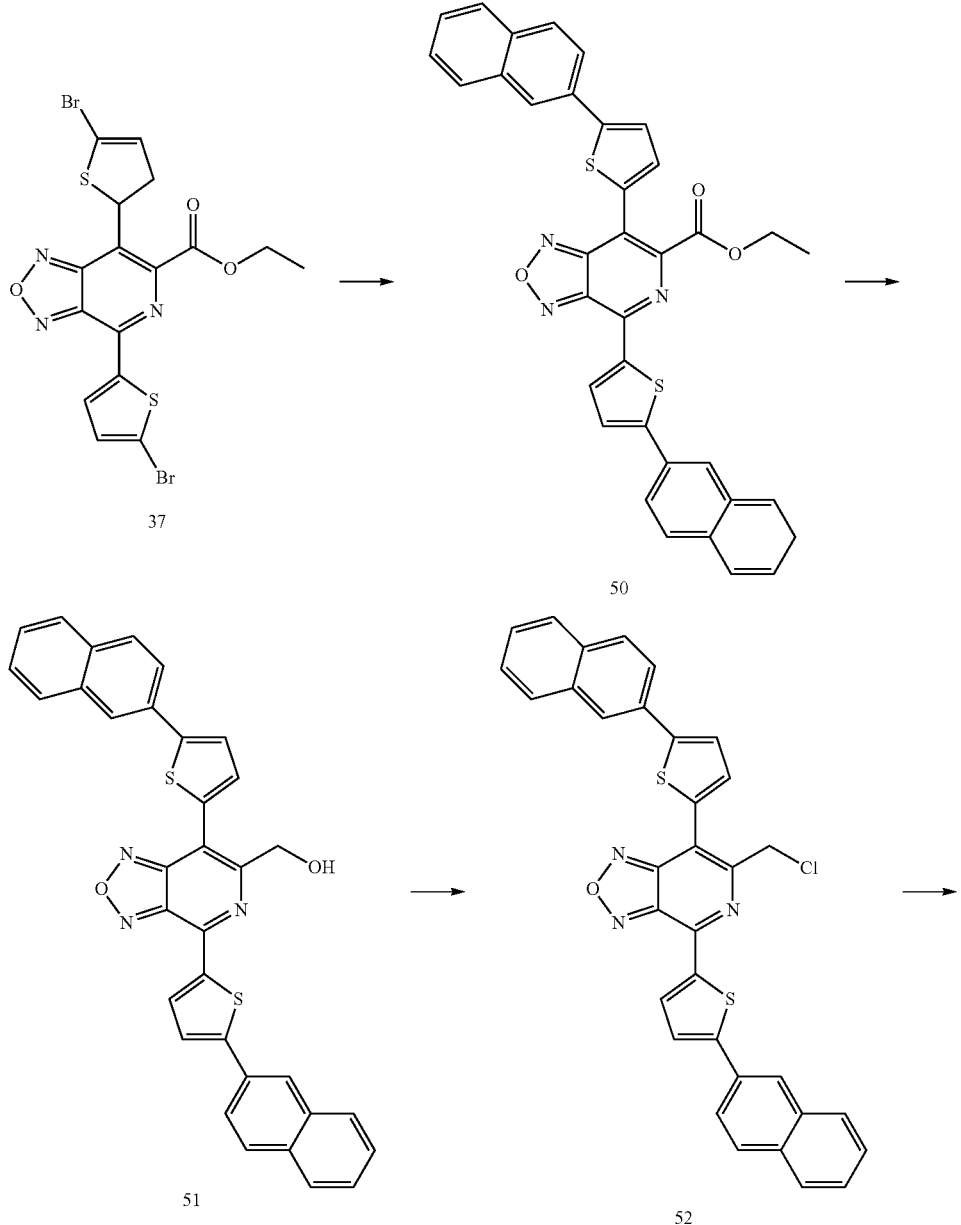

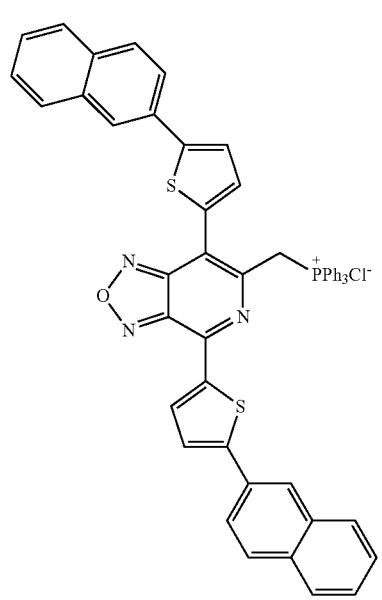

53

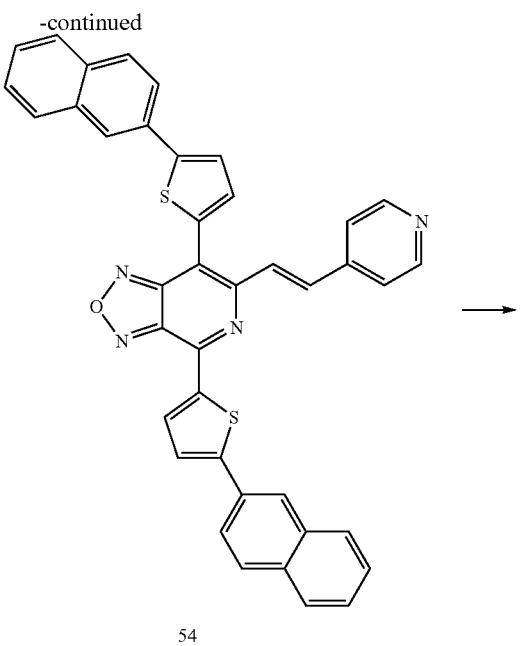

54

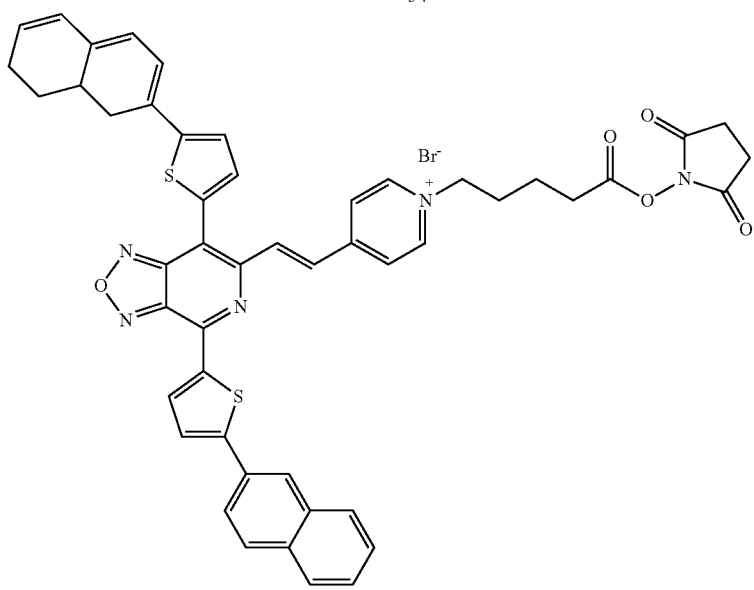

55

(1) Synthesis of an Ethyl Ester (50)

In an eggplant flask in which the atmosphere was replaced with argon, 232 mg (0.45 mmol) of the ethylester (37) and 15 mg of tetrakis triphenylphosphine palladium were placed and dissolved in 3 ml of 2M-sodium carbonate and 4.5 ml of benzene. In 2.5 ml of ethanol, 166 mg (0.96 mmol) of 2-naphthylboronic acid was dissolved, and the obtained mixture was poured into the reaction solution. Thereafter, the reaction solution was refluxed under heating at 80° C. for 7 hours. Into the reaction solution, 15 ml of water was poured for extraction using chloroform. Chloroform was distilled off under reduced pressure and the residue was recrystallized from hexane-chloroform. An ethyl ester (50) was thus obtained in a yield amount of 176 mg and in a yield of 64%.

(2) Synthesis of a Hydroxymethyl (51)

A solution of DIBAL (manufactured by Sigma Aldrich, concentration 1.5 M, 5 μL) in toluene was added dropwise to a solution (3 ml) of the ethyl ester (50) (250 mg, 0.41 mmol) in THF under ice-cooling, and the mixture was stirred under ice-cooling for 30 minutes, and subsequently at room temperature for 60 minutes. Then, the reaction solution was poured into water, which was put into an acidic state (precipitate disappeared) by adding an aqueous 3% HCl to be extracted with chloroform. The extract was dried over MgSO$_4$, and the residue obtained after distillation under reduced pressure was dispersed in silica gel (Kanto C-60), which was then heated at 80° C. overnight. This silica gel was washed with ethyl acetate (AcOEt), and the residue obtained by distilling the washed solution under reduced pressure was subjected to column treatment (Kanto C-60, Hexane/AcOEt=2/1 (v/v)) to obtain a hydroxymethyl (51) in a yield amount of 95 mg and in a yield of 41%.

(3) Synthesis of a Chloromethyl (52)

A solution (6 ml) of the hydroxymethyl (51) (200 mg) and SOCl$_2$ (6 ml) in chloroform was refluxed under heating for 2 hours. The reaction solution was poured into water, which was neutralized with NaHCO$_3$ and then extracted with chloroform. The extract was dried over MgSO$_4$ and the residue obtained after distillation under reduced pressure was subjected to column treatment (Kanto C-60; Hexane/CHCl$_3$=5/1 (v/v)) to obtain a chloromethyl (52) in a yield amount of 201 mg.

(4) Synthesis of a Phosphonium Salt (53)

A solution (3 ml) of the chloromethyl (52) (100 mg, 0.17 mmol) and Ph$_3$P (49 mg, 0.19 mmol) in toluene was refluxed under heating for 24 hour. The precipitate was filtrated to obtain a phosphonium salt (53) in a yield amount of 61 mg and in a yield of 42%.

(5) Synthesis of a Vinyl (54)

p-Formylpyridine (21 μL, 0.31 mmol) was added to a solution (3 ml) of the phosphonium salt (53) (170 mg, 0.20 mmol) and potassium hydroxide (purity: 85%, 30 mg) in ethanol under ice-cooling, and the mixture was stirred at the temperature for 1 hour and subsequently at room temperature for 45 minutes. The precipitate was filtrated and subjected to column treatment (Kanto C-60; CHCl$_3$/AcOEt=10/1 (v/v)) to obtain a vinyl (54) in a yield amount of 83 mg and in a yield of 65%.

(6) Synthesis of an Active Ester (55)

A solution (2.5 ml) of the vinyl (54) (150 mg, 0.23 mmol) and a bromohexanoic acid active ester (75 mg, 0.26 mmol) in toluene was refluxed under heating for 2 days. The precipitate was filtrated to obtain an active ester (55) of a pyridinium salt.

Synthetic Example 20

An example of synthesis of an active ester of 4,7-di[(2-biphenyl)thienyl]-1,2,5-oxadiazolopyridine-6-(4-pyridinium) will be shown below.

Scheme 27

[Chemical Formula 33]

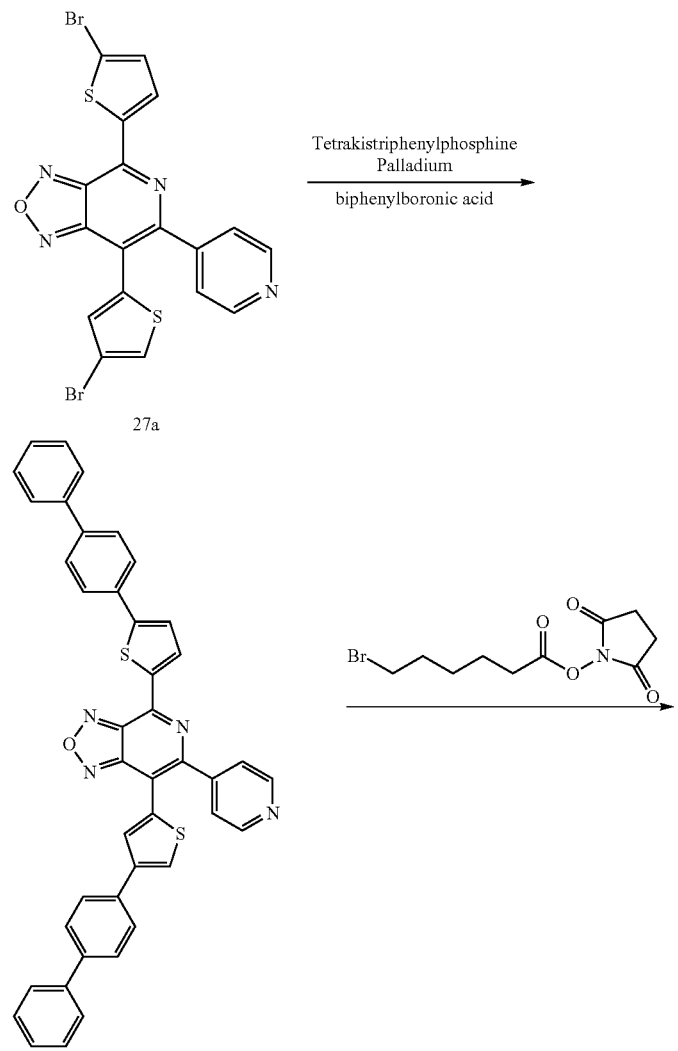

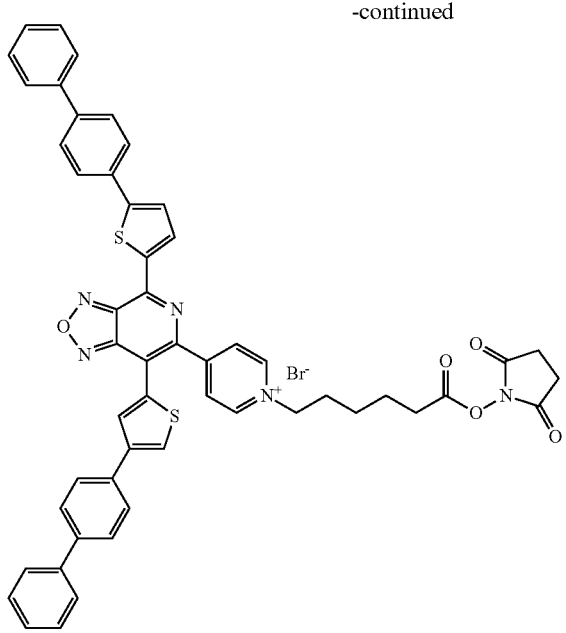

57

(1) Synthesis of a Pyridyl (56) Using Suzuki Coupling in an eggplant flask in which the atmosphere was replaced with argon, 200 mg (0.38 mmol) of the pyridyl (27a) and 12.7 mg of tetrakis triphenylphosphine palladium were placed and dissolved in 2.8 ml of an aqueous 2M-sodium carbonate solution and 4 ml of benzene. In 2 ml of ethanol, 164 mg (0.83 mmol) of biphenylboronic acid was dissolved, and the obtained mixture was poured into the reaction solution. Thereafter, the reaction solution was refluxed under heating at 80° C. for 5 hours. Into the reaction solution, 20 ml of water was poured for extraction using chloroform. Chloroform was distilled off under reduced pressure and the residue was recrystallized from hexane-chloroform. A pyridyl (56) was thus obtained in a yield amount of 155 mg and in a yield of 61%.

(2) Synthesis of an Active Ester (57)

In 8 ml of toluene, the pyridyl (56) (300 mg, 0.45 mmol) and 145 mg of a bromohexanoic acid active ester (0.49 mmol) were dissolved, and the obtained mixture was then stirred at room temperature overnight. After the reaction was completed, the reaction mixture was subjected to suction filtration and the filtrated product was dried under vacuum to obtain an active ester (57).

Synthetic Example 21

An example of synthesis of an active ester of 4,7-di[(2-biphenyl)thienyl]-1,2,5-oxadiazolopyridine-6-(4-vinylpyridinium) will be shown below.

Scheme 28

[Chemical Formula 34]

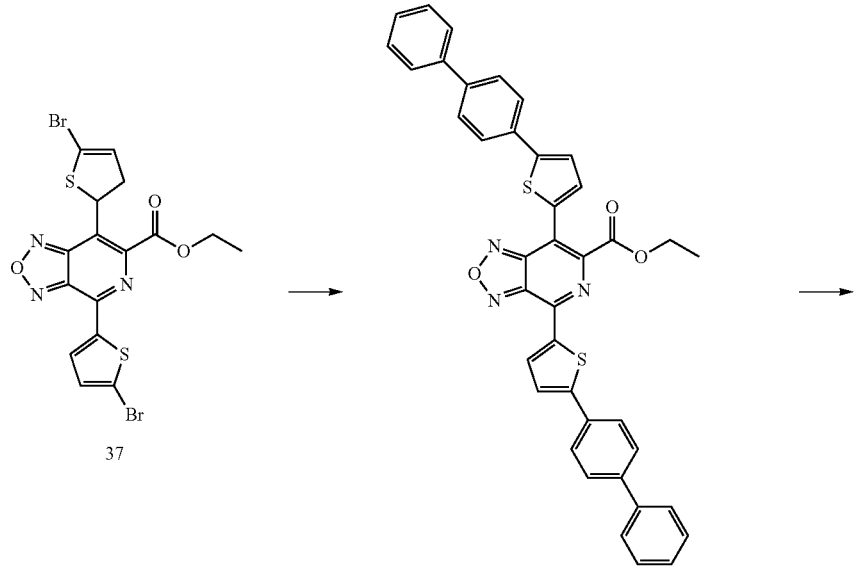

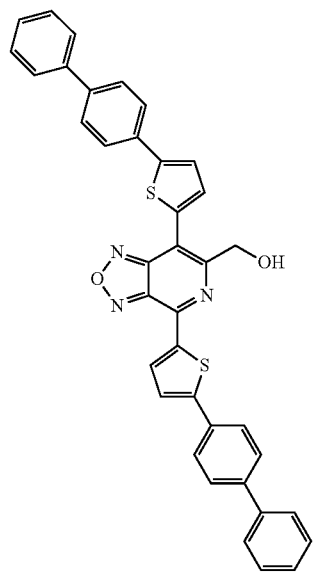
59
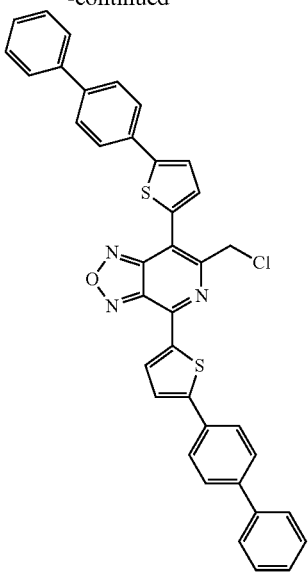
60
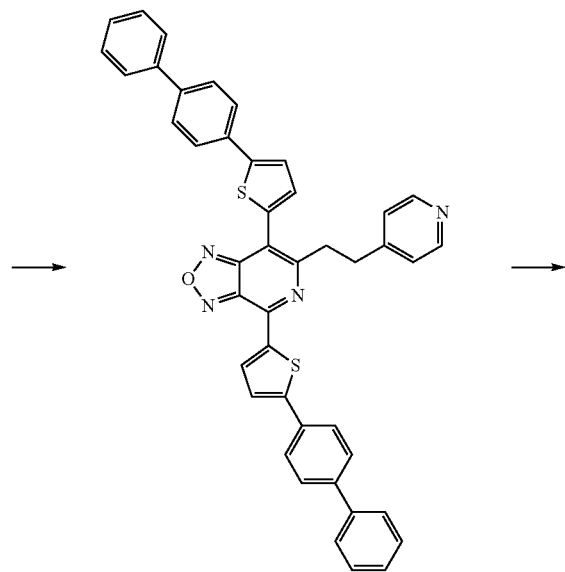

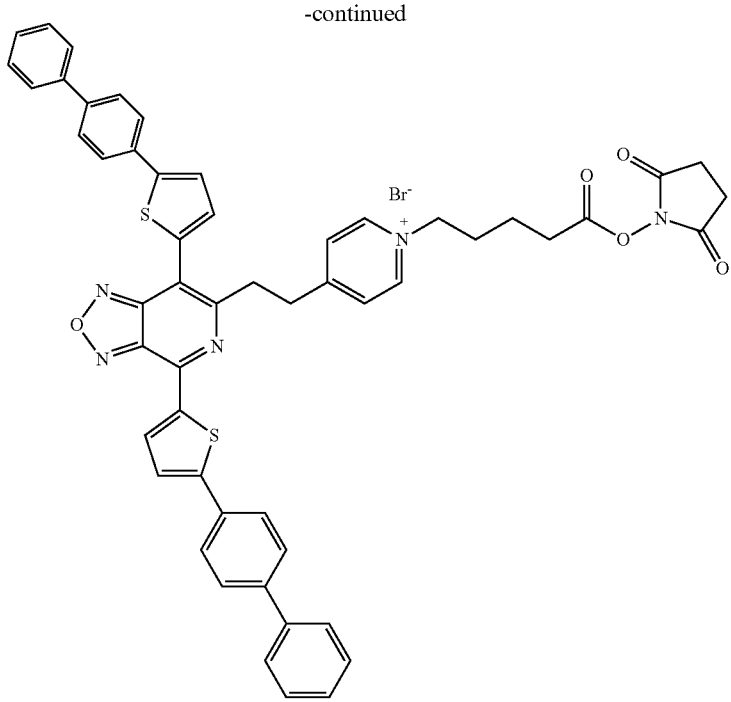

63

(1) Synthesis of a Pyridyl (33) Using Suzuki Coupling

In an eggplant flask in which the atmosphere was replaced with argon, 200 mg (0.39 mmol) of the pyridyl (37) and 14 mg of tetrakis triphenylphosphine palladium were placed and dissolved in 3 ml of 2M-sodium carbonate and 4.5 ml of benzene. In 2.5 ml of ethanol, 140 mg (0.81 mmol) of 2-naphthylboronic acid was dissolved, and the obtained mixture was poured into the reaction solution. Thereafter, the reaction solution was refluxed under heating at 80° C. for 7 hours. Into the reaction solution, 15 ml of water was poured for extraction using chloroform. Chloroform was distilled off under reduced pressure and the residue was recrystallized from hexane-chloroform. A pyridyl (58) was thus obtained in a yield amount of 165 mg and in a yield of 64%.

(2) Synthesis of a Hydroxymethyl (59)

A solution of DIBAL (manufactured by Sigma Aldrich, concentration 1.5 M, 7 μL) in toluene was added dropwise to a solution (3 ml) of the ethyl ester (58) (290 mg, 0.44 mmol) in THF under ice-cooling, and the mixture was stirred under ice-cooling for 30 minutes, and subsequently at room temperature for 60 minutes. Then, the reaction solution was poured into water, which was put into an acidic state (precipitate disappeared) by adding an aqueous 3% HCl to be extracted with chloroform. The extract was dried over MgSO₄, and the residue obtained after distillation under reduced pressure was dispersed in silica gel (Kanto C-60), which was then heated at 80° C. overnight. This silica gel was washed with ethyl acetate (AcOEt), and the residue obtained by distilling the washed solution under reduced pressure was subjected to column treatment (Kanto C-60, Hexane/AcOEt=2/1 (v/v)) to obtain a hydroxymethyl (59) in a yield amount of 112 mg and in a yield of 41%.

(3) Synthesis of a Chloromethyl (60)

A solution (6 ml) of the hydroxymethyl (59) (200 mg) and SOCl₂ (6 ml) in chloroform was refluxed under heating for 2 hours. The reaction solution was poured into water, which was neutralized with NaHCO₃ and then extracted with chloroform. The extract was dried over MgSO₄ and the residue obtained after distillation under reduced pressure was subjected to column treatment (Kanto C-60; Hexane/CHCl₃=5/1 (v/v)) to obtain a chloromethyl (60) in a yield amount of 201 mg.

(4) Synthesis of a Phosphonium Salt (61)

A solution (3 ml) of the chloromethyl (60) (100 mg, 0.16 mmol) and Ph₃P (45 mg, 0.17 mmol) in toluene was refluxed under heating for 24 hours. The precipitate was filtrated to obtain a phosphonium salt (61) in a yield amount of 61 mg and in a yield of 42%.

(5) Synthesis of a Vinyl (62)

p-Formylpyridine (29 μL, 0.31 mmol) was added to a solution (3 ml) of the phosphonium salt (61) (252 mg, 0.28 mmol) and potassium hydroxide (purity: 85%, 30 mg) in ethanol under ice-cooling, and the mixture was stirred at the temperature for 1 hour and subsequently at room temperature for 45 minutes. The precipitate was filtrated and subjected to column treatment (Kanto C-60; CHCl₃/AcOEt=10/1 (v/v)) to obtain a vinyl (62) in a yield amount of 126 mg and in a yield of 65%.

(6) Synthesis of an Active Ester (63)

A solution (2.5 ml) of the vinyl (62) (150 mg, 0.22 mmol) and a bromohexanoic acid active ester (69 mg, 0.24 mol) in toluene was refluxed under heating for 2 days. The precipitate was filtrated to obtain an active ester (63) of a pyridinium salt.

Synthetic Example 22 (Comparative Example)

For comparison, an active ester of 4,7-diphenyl-1,2,5-oxadiazolopyridine ethyl ester was synthesized.

In a 50 ml three-neck flask, 1.0 g (1.6 mmol) of the ester (4) obtained in Synthetic Example 1 was dissolved in 30 ml of ethanol. To this, 0.11 g (3.0 mmol) of KOH was added. The mixture was refluxed under heating for 5 hours, and then the reaction mixture was poured into 50 ml of water. The pH of the aqueous solution was adjusted to 1 by hydrochloric acid to obtain a precipitate. The precipitate was recrystallized from water-ethanol (1:1) to obtain a carboxylic acid (yield amount: 0.47 g, yield: 81%).

In a 50 ml three-neck flask, 70 mg (0.17 mmol) of the carboxylic acid and 21 mg (0.18 mmol) of N-hydroxysuccinimide were dissolved in 20 ml of DMF. To this, 37 mg (0.17 mmol) of N,N'-dicyclohexylcarbodiimide dissolved in 5 ml of DMF was added dropwise over 30 minutes. After the dropwise addition, the solution was stirred at room temperature for 30 hours. DMF was distilled off under reduced pressure. The residue was isolated by silica gel column chromatography to obtain an active ester (yield amount: 90 mg, yield: 78%).

Measurement of a Fluorescence Spectrum
(Measurement Method)

Each of the synthesized fluorescent dyes was dissolved in a solvent by using DMSO to prepare a solution having a concentration of $10^{-4}$ M, so that the measurements of fluorescent wavelength and absorption wavelength were performed.

TABLE 1

|  | Absorption wavelength (nm) | Fluorescence wavelength (nm) | Stokes shift (nm) |
| --- | --- | --- | --- |
| Synthetic Example 1 | 411 | 531 | 120 |
| Synthetic Example 2 | 437 | 608 | 171 |
| Synthetic Example 3 | 402 | 511 | 109 |
| Synthetic Example 4 | 412 | 518 | 106 |
| Synthetic Example 5 | 409 | 517 | 108 |
| Synthetic Example 6 | 415 | 528 | 113 |
| Synthetic Example 7 | 418 | 532 | 114 |
| Synthetic Example 8 | 416 | 535 | 119 |
| Synthetic Example 9 | 539 | 660 | 121 |
| Synthetic Example 10 | 531 | 650 | 119 |
| Synthetic Example 11 | 528 | 648 | 120 |
| Synthetic Example 12 | 382 | 513 | 131 |
| Synthetic Example 13 | 516 | 698 | 182 |
| Synthetic Example 14 | 500 | 710 | 210 |
| Synthetic Example 15 | 532 | 722 | 190 |
| Synthetic Example 16 | 516 | 682 | 166 |
| Synthetic Example 17 | 509 | 688 | 179 |
| Synthetic Example 18 | 535 | 700 | 165 |
| Synthetic Example 19 | 533 | 730 | 197 |
| Synthetic Example 20 | 529 | 715 | 186 |
| Synthetic Example 21 | 404 | 527 | 123 |

(Result)

The fluorescent dyes obtained in Synthetic Examples 1 to 21 were each directly soluble in water. Contrary to this, the fluorescent dye of Synthetic Example 22 which had neither a nitrogen cation-containing group nor a nitrogen-containing group could not be directly dissolved in water. A stokes shift of 100 nm or more was obtained in all the synthesized fluorescent dyes. An absorption wavelength of 400 to 450 nm was obtained in the 4,7-diphenyl whereas an absorption wavelength of 500 nm or more and a fluorescence wavelength of 600 nm or more were obtained in the 4,7-thienyl. When the fluorescence intensity of Synthetic Example 22 was 1.0, a very high fluorescence intensity as much as 11.2 was obtained in Synthetic Example 1 and a very high fluorescence intensity as much as 6.0 was obtained in Synthetic Example 12.

Biological Specimen Observation
(Specimen Production Method)

The kidney of a 7-year-old Wister rat was fixed by perfusion using 4% Para formaldehyde, 0.03% glutaraldehyde, and 0.1 M cacodylic acid buffer solution. After the perfusion fixation, the kidney was extracted and subjected to postfixation using 4% paraformaldehyde. Next, the sample was immersed in a 25% hypertonic sucrose solution (solvent: KPBS) for 2 hours so as to avoid a freezing damage to the specimen, and then embedded with an embedding agent to freeze the sample in a deep freezer kept at −80° C. After freezing, a 8-μm frozen section was made by a cryostat set at −20° C. and applied to a slide glass. The obtained sample was washed three times with PBS for 20 minutes. Biotinylated lectin was added to the sample at room temperature for 1 day. Next, after being washed three times with PBS for 10 minutes, the sample was dyed using a fluorescently labeling streptavidin for 3 hours. After being dyed, the sample was washed with PBS, encapsulated with a water-soluble encapsulating agent, and then observed with a fluorescence microscope.

(Result)

Figure 2:
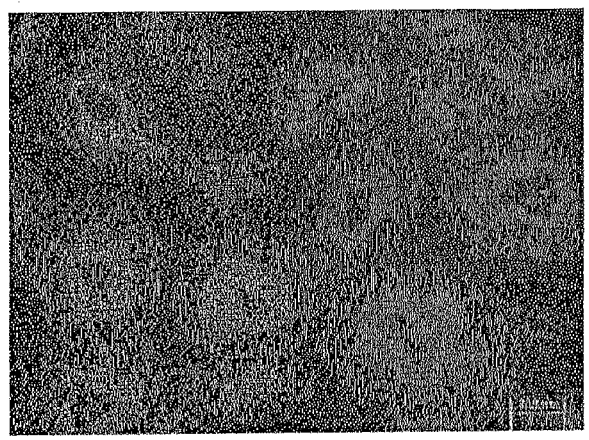
FIG. 2 is a fluorescence micrograph of a specimen produced using a conventional fluorescent dye.

FIG. 1 shows an example dyed using the fluorescent dye of Synthetic Example 9 and FIG. 2 shows an example dyed using Texas Red for comparison. In the case of Texas Red, the external side of a renal tubule was dyed because of nonspecific adsorption, whereas in the case of the fluorescent dye of Synthetic Example 9, the dye was not adsorbed to the external side at all and only the inside of the renal tubule brush border was dyed. The shape of the inside of the renal tubule brush border could be clearly observed without any blurring.

What is claimed is:

1. A fluorescent dye comprising an azole derivative represented by the following general formula (1):

[Chemical Formula 1]

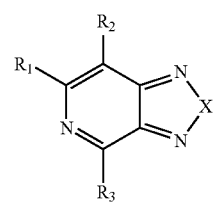

(1)

wherein $R_1$ in the formula (1) is represented by the general formula $L_1$-$M_1$, wherein $M_1$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_1$ represents a linker which is represented by —(CH=$CR_6$)$_n$— and which connects $M_1$ with a center pyridine ring, n represents an integer of from 1 to 5, $R_6$ represents any one of a hydrogen atom; a linear or branched alkyl group which may have a substituent and has 1 to 6 carbon atoms; a sulfo group which may have a substituent; a heterocyclic group selected from the group consisting of an imidazolium group, a pyridinium group, and a furan group, each of which may have a substituent; an amino group selected from the group consisting of a secondary amino group, a tertiary amino group, and a quaternary amino group, each of which may have a substituent; a hydroxy group which may have a substituent; an alkoxy group which may have a substituent; an aldehyde group which may have a substituent; a carboxyl group which may have a substituent;

and an aromatic group which may have a substituent, $R_2$ and $R_3$ in the formula (1) each independently represent a hydrogen atom, a halogen atom, or an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and $An^-$ represents a halide ion, $CF_3SO_3^-$, $BF_4^-$, or $PF_6^-$.

2. The fluorescent dye according to claim 1, wherein $R_2$ and $R_3$ above are each independently a thienyl group, a furanyl group, a pyrrolyl group, an imidazolyl group, an oxazolyl group, a thiadiazolyl group, a pyrazolyl group, a pyridyl group, or a quinolyl group, each of which may have a substituent.

3. The fluorescent dye according to claim 2, wherein $R_2$ and $R_3$ each represent a thienyl group which may have a substituent, wherein the substituent is an aromatic hydrocarbon group, an aliphatic hydrocarbon group, or a heterocyclic group, each of which may have a substituent.

4. A fluorescent dye comprising an azole derivative represented by the following general formula (4):

[Chemical Formula 2]

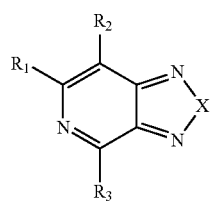

(4)

wherein $R_1$ in the formula (4) is represented by the general formula $L_2$-$M_2$, wherein $M_2$ represents a nitrogen cation-containing group such as a pyridinium group, a secondary aminium group, a tertiary aminium group, a quaternary ammonium group, a piperidinium group, a piperazinium group, an imidazolium group, a thiazolium group, an oxazolium group, a quinolium group, a benzoimidazolium group, a benzothiazolium group, or a benzooxazolium group, each of which may have a substituent, or a nitrogen-containing group such as a pyridyl group, a secondary amino group, a tertiary amino group, a piperidyl group, a piperadyl group, an imidazolyl group, a thiazolyl group, an oxazolyl group, a quinolyl group, a benzoimidazolyl group, a benzothiazolyl group, or a benzooxazolyl group, each of which may have a substituent, $L_2$ represents a linker which connects $M_2$ with a center pyridine ring and which represents a direct bond or one or more types of functional groups selected from the group consisting of —$(CH_2)_n$— (n represents an integer of from 1 to 4), —NHCOO—, —CONH—, —COO—, —$SO_2$NH—, —HN—C(=NH)—NH—, —O—, —S—, —NR (R represents an alkyl group), —Ar— (Ar represents an aromatic hydrocarbon group), and —CO—Ar—NR—, $R_2$ and $R_3$ in the formula (4) each independently represent a thienyl group which may have a substituent, wherein the substituent is an aromatic hydrocarbon group, an aliphatic hydrocarbon group, or a heterocyclic group, each of which may have a substituent, X represents a nitrogen atom, a sulfur atom, an oxygen atom, a selenium atom, or a boron atom, each of which may have a substituent, R' represents an aliphatic hydrocarbon group or an aromatic hydrocarbon group including an alkyl group which may have an aromatic ring, and $An^-$ represents a halide ion, $CF_3SO_3^-$, $BF_4^-$, or $PF_6^-$.

* * * * *